United States Patent
Siejko

(10) Patent No.: US 9,895,071 B2
(45) Date of Patent: *Feb. 20, 2018

(54) CARDIAC RATE TRACKING IN AN IMPLANTABLE MEDICAL DEVICE

(71) Applicant: CAMERON HEALTH, INC., St. Paul, MN (US)

(72) Inventor: Krzysztof Z. Siejko, Maple Grove, MN (US)

(73) Assignee: CAMERON HEALTH, INC., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/254,883

(22) Filed: Sep. 1, 2016

(65) Prior Publication Data

US 2016/0367829 A1 Dec. 22, 2016

Related U.S. Application Data

(63) Continuation of application No. 14/819,817, filed on Aug. 6, 2015, now Pat. No. 9,451,892.

(Continued)

(51) Int. Cl.
*A61N 1/39* (2006.01)
*A61B 5/0456* (2006.01)
(Continued)

(52) U.S. Cl.
CPC ........ *A61B 5/04012* (2013.01); *A61B 5/0245* (2013.01); *A61B 5/04014* (2013.01); *A61B 5/0422* (2013.01); *A61B 5/0456* (2013.01); *A61B 5/04525* (2013.01); *A61B 5/4836* (2013.01); *A61B 5/686* (2013.01); *A61B 5/7246* (2013.01); *A61N 1/3704* (2013.01); *A61N 1/3925* (2013.01); *A61N 1/3956* (2013.01);

(Continued)

(58) Field of Classification Search
None
See application file for complete search history.

(56) References Cited

U.S. PATENT DOCUMENTS 3,811,428 A 5/1974 VanHorn et al.
4,239,048 A 12/1980 Steuer
(Continued)

FOREIGN PATENT DOCUMENTS

WO 2012135062 A1 10/2012
WO 2013160538 A1 10/2013

OTHER PUBLICATIONS

"Invitation to Pay Additional Fees, and where Applicable, Protest Fee," Application No. PCT/2015/045158 dated Jan. 13, 2016.
(Continued)

*Primary Examiner* — Kennedy Schaetzle
(74) *Attorney, Agent, or Firm* — Seager, Tufte & Wickhem LLP

(57) ABSTRACT

Self-correlation enhancements and implementations are described. In particular, certain examples demonstrate the use of a tracking mechanism to identify and/or confirm cardiac rate using data from iterative self-correlation performed at intervals over time. This may enable the interpolation of cardiac rate in an implantable medical device when data is insufficient, and may provide confidence in cardiac rate analyses.

20 Claims, 19 Drawing Sheets

Related U.S. Application Data

(60) Provisional application No. 62/038,437, filed on Aug. 18, 2014, provisional application No. 62/038,440, filed on Aug. 18, 2014, provisional application No. 62/038,438, filed on Aug. 18, 2014.

(51) Int. Cl.
| | |
|---|---|
| *A61B 5/04* | (2006.01) |
| *A61B 5/042* | (2006.01) |
| *A61B 5/00* | (2006.01) |
| *A61B 5/0245* | (2006.01) |
| *A61B 5/0452* | (2006.01) |
| *G06F 17/16* | (2006.01) |
| *A61N 1/37* | (2006.01) |
| *A61B 5/046* | (2006.01) |
| *A61B 5/0464* | (2006.01) |

(52) U.S. Cl.
CPC ........... *A61N 1/3987* (2013.01); *G06F 17/16* (2013.01); *A61B 5/046* (2013.01); *A61B 5/04011* (2013.01); *A61B 5/0464* (2013.01)

(56) References Cited

U.S. PATENT DOCUMENTS

| | | | |
|---|---|---|---|
| 5,243,993 A | 9/1993 | Alexander et al. | |
| 5,558,096 A | 9/1996 | Palatnik | |
| 5,709,215 A | 1/1998 | Perttu et al. | |
| 5,807,267 A | 9/1998 | Bryars et al. | |
| 6,312,382 B1 | 11/2001 | Mucci et al. | |
| 6,567,691 B1 | 5/2003 | Stadler | |
| 6,647,292 B1 | 11/2003 | Bardy et al. | |
| 6,721,597 B1 | 4/2004 | Bardy et al. | |
| 7,149,575 B2 | 12/2006 | Ostroff et al. | |
| 7,194,302 B2 | 3/2007 | Bardy et al. | |
| 7,248,921 B2 | 7/2007 | Palreddy et al. | |
| 7,623,909 B2 | 11/2009 | Sanghera et al. | |
| 7,869,863 B2 * | 1/2011 | Moses | A61B 5/02411 600/511 |
| 8,160,686 B2 | 4/2012 | Allavatam et al. | |
| 8,160,687 B2 | 4/2012 | Warren et al. | |
| 8,200,341 B2 | 6/2012 | Sanghera et al. | |
| 8,265,737 B2 | 9/2012 | Warren et al. | |
| 8,409,107 B2 | 4/2013 | Sweeney et al. | |
| 8,521,276 B2 | 8/2013 | Sweeney et al. | |
| 8,565,878 B2 | 10/2013 | Allavatam et al. | |
| 8,744,555 B2 | 6/2014 | Allavatam et al. | |
| 9,451,892 B2 * | 9/2016 | Siejko | A61N 1/3704 |
| 2004/0042581 A1 | 3/2004 | Okerlund | |
| 2010/0016693 A1 | 1/2010 | Addison | |
| 2013/0079657 A1 | 3/2013 | Ochs et al. | |
| 2014/0073960 A1 | 3/2014 | Rodriguez-Llorente et al. | |
| 2014/0180154 A1 | 6/2014 | Sierra et al. | |
| 2014/0275854 A1 | 9/2014 | Venkatraman | |
| 2014/0278229 A1 | 9/2014 | Hong | |
| 2015/0112606 A1 | 4/2015 | He et al. | |

OTHER PUBLICATIONS

"Notification of Transmittal of the International Search Report and the Written Opinion of the International Searching Authority, or the Declaration," International Application No. PCT/US2015/045157, dated Oct. 19, 2015.

PCT Appl. No. US2015/045157, The International Search Report and the Written Opinion of the International Searching Authority, dated Oct. 19, 2015.

\* cited by examiner

CARDIAC RATE TRACKING IN AN IMPLANTABLE MEDICAL DEVICE

CROSS-REFERENCE TO RELATED PATENT DOCUMENTS

The present application is a continuation of U.S. application Ser. No. 14/819,817, filed on Aug. 6, 2015, now U.S. Pat. No. 9,451,892, titled CARDIAC RATE TRACKING IN AN IMPLANTABLE MEDICAL DEVICE, which claims the benefit of and priority to each of U.S. Provisional Patent Application No. 62/038,440, filed on Aug. 18, 2014, and titled CALCULATION OF SELF-CORRELATION IN AN IMPLANTABLE CARDIAC DEVICE, U.S. Provisional Patent Application No. 62/038,437, filed Aug. 18, 2014, and titled CARDIAC RATE TRACKING IN AN IMPLANTABLE MEDICAL DEVICE, and U.S. Provisional Patent Application No. 62/038,438, filed Aug. 18, 2014, and titled PEAK SELECTION FOR SELF CORRELATION ANALYSIS OF CARDIAC RATE IN AN IMPLANTABLE MEDICAL DEVICE, the disclosures of which are incorporated herein by reference. The present application is also related to U.S. Pat. No. 9,451,893, titled CALCULATION OF SELF-CORRELATION IN AN IMPLANTABLE CARDIAC DEVICE, and U.S. Pat. No. 9,629,565, titled PEAK SELECTION FOR SELF CORRELATION ANALYSIS OF CARDIAC RATE IN AN IMPLANTABLE MEDICAL DEVICE, the disclosures of which are incorporated herein by reference

BACKGROUND

Implantable defibrillators are designed to deliver an electrical stimulus to terminate certain deleterious arrhythmias. They must detect dangerous arrhythmias with a high rate of success (sensitivity). They must also avoid delivering electrical stimulus when not desired (specificity). Attaining high sensitivity and specificity in the discrimination of such deleterious arrhythmias is a challenge.

Typically treatable arrhythmias include ventricular fibrillation (VF) and/or polymorphic ventricular tachycarrhythmia (PVT). Other arrhythmias can include monomorphic ventricular tachyarrhythmia (MVT), atrial fibrillation (AF), and atrial flutter (Flutter), with the atrial arrhythmias of AF and Flutter deemed supraventricular tachyarrhythmias (SVT). For some patients, MVT is treated by the implantable defibrillator using anti-tachycardia pacing (ATP), while AF and Flutter are typically addressed by other therapies entirely. In addition, patients can experience exercise induced ventricular tachycardia (VT), which is typically not treated at all. Some patients experience bundle branch blocks and other conditions that can arise at elevated rates, causing the signal shape (morphology) of the cardiac signal with each cardiac beat to change relative to morphology at slower rates. Implantable devices are expected to appropriately distinguish these various conditions and apply the correct therapy for only certain conditions.

Chen et al., in Ventricular Fibrillation Detection By A Regression Test On The Autocorrelation Function, *Med Biol Eng Comput.;* 25 (3): 241-9 (May, 1987), discuss the use of an autocorrelation function (ACF) to identify ventricular fibrillation in which the ACF is performed. Chen et al. hypothesize that the peaks in the ACF output are expected to be periodic and/or regular and should pass a linear regression test when a ventricular tachycardia (VT) is occurring. Therefore, the results of the ACF are subjected to a linear regression analysis and VF is declared if the linear regression fails to find a linear fit. Chen et al. limit their analysis to VF and VT and do not address the fact that the linear regression they discuss would also likely fail for supraventricular arrhythmias such as atrial flutter or atrial fibrillation for which defibrillation therapy is typically not desired. Moreover, adding a linear regression test with ACF would create a very large computational burden for an implantable system.

Sweeney et al., in U.S. Pat. Nos. 8,409,107 and/or 8,521,276 discuss the use of an ACF applied to a transformation of detected cardiac signal using curve matching. The ACF would be applied to identify recurring curves. Such recurring curves could be used to find heart beats from the transformed signal, which could be used to calculate rate. ACF is not directly applied to the time varying cardiac signal, however.

ACF in each of these examples involves a large number of computational steps to be calculated. To make ACF more useful in an implantable device, simplified methods and alternative methods which address the spectrum of potential arrhythmias are desired.

Overview

The present inventor has recognized, among other things, that a problem to be solved can include the incorporation of a modified autocorrelation function into an implantable cardiac device. Modifications can be made to reduce the computational burden of the correlation function and accommodate some of the difficulties which arise in the context of an implantable device monitoring cardiac function. The present subject matter can help provide a solution to the problem of enhancing sensitivity and specificity in implantable cardiac rhythm management devices.

The present invention comprises several separately implementable elements which provide avenues for reliable use of ACF at lesser computational burden in an implantable device.

In a first aspect, the invention comprises a set of rules for the calculation of a Minimum Absolute Difference (MAD) function to construct a Self-correlation. The use of MAD facilitates a far simpler and less computationally intensive manner of analyzing the cardiac signal than ACF.

In a second aspect, the invention comprises a set of rules for the identification and selection of candidate peaks within a Self-correlation or ACF to yield an estimate of heart rate.

In a third aspect, the present invention comprises a set of rules for tracking cardiac rate over time using output peaks from either a Self-correlation or ACF.

The first, second and third aspects may each be used independent of the other aspects, or in any suitable combination such as first-second, first-third, or second-third.

In a fourth aspect, the present invention comprises an integrated system or method in which a simplified Self-correlation of the first aspect is combined with the second and third aspects.

In various embodiments, devices and methods may use any of the first through fourth aspects either on a continuing basis or following a triggering event.

The present disclosure is, in certain examples, directed to enhancements that enable rate tracking using the results of a self-correlation function. The self-correlation function can take the form of a simplified ACF, such as an MAD, including for example methods of U.S. Provisional Patent Application No. 62/038,440, titled CALCULATION OF SELF-CORRELATION IN AN IMPLANTABLE CARDIAC DEVICE. Intermediate analysis, such as that in U.S.

Provisional Patent Application No. 62/038,438, titled PEAK SELECTION FOR SELF-CORRELATION ANALYSIS OF CARDIAC RATE IN AN IMPLANTABLE MEDICAL DEVICE, can provide a set of results to the rate tracking enhancement. However, other examples simply make use of a data set including one or more possible rates and, when justified, an estimated rate. For example, a full version of ACF may be used rather than a simplified or lower power version.

The rate tracking enhancement is designed to stabilize the output rate estimation in the face of challenges such as the occasional premature ventricular contraction (PVC) or other ventricular extra-systole beat, bigemini rhythms, changes in the cardiac signal due to posture, muscle artifact, respiration, bundle branch block, and external noise, among others. Such challenges can make the provision of a confident rate estimate intermittent, such that choices must be made between possible rates and/or the potential to determine that the data set does not enable a high-confidence rate calculation.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
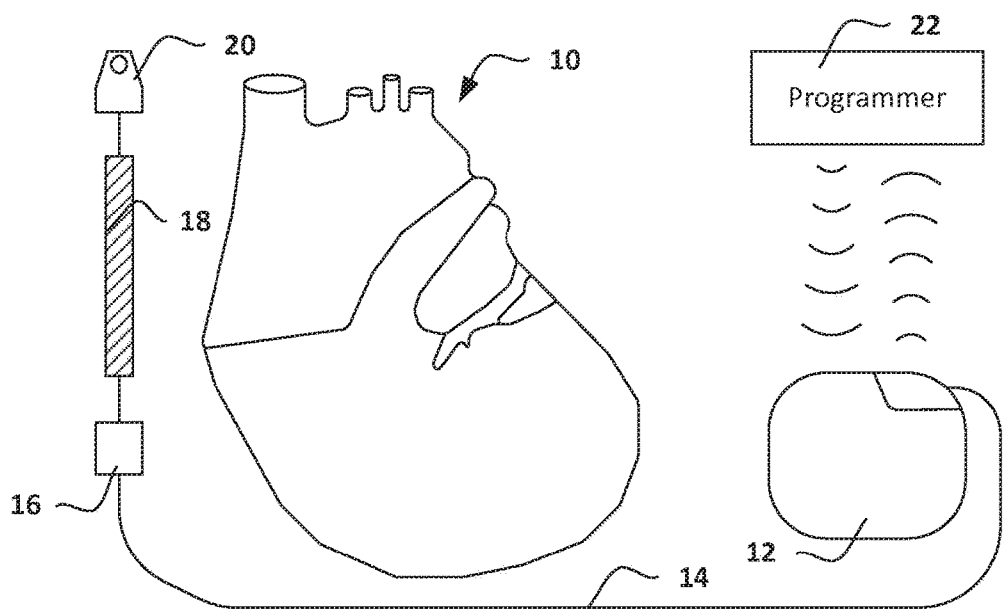
FIG. 1 shows a subcutaneously implanted cardiac treatment system.
Figure 2:
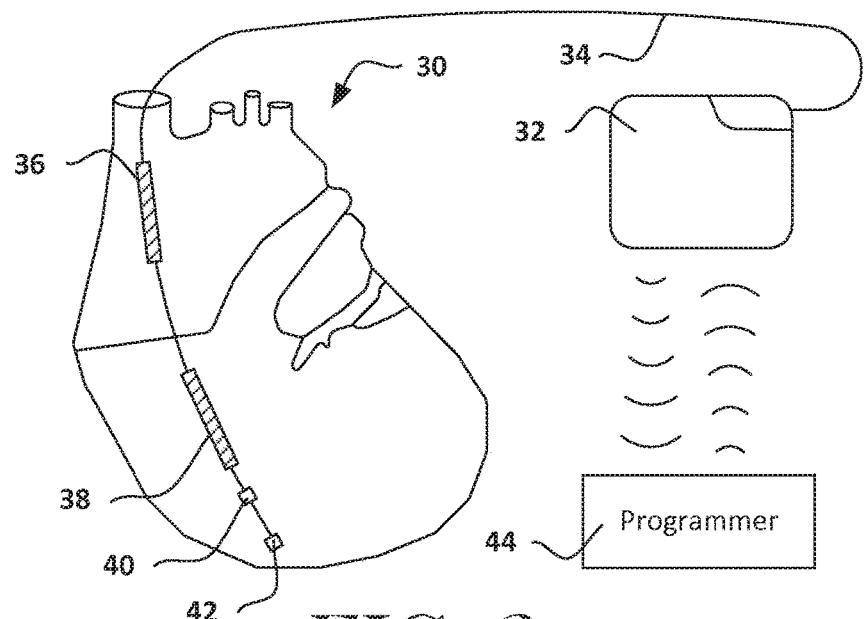
FIG. 2 shows a transvenously implanted cardiac treatment system.

FIGS. 1-2 show implant locations for illustrative cardiac systems. The present invention may find application in a subcutaneous-only system as illustrated in FIG. 1, or in a transvenous system as shown in FIG. 2. Alternatives may include systems having multiple subcutaneous, transvenous and/or intracardiac elements, epicardial systems, or fully intravenous or intracardiac systems.

The illustrative system shown in FIG. 1 is shown relative to a heart 10 and is intended to convey a subcutaneous implant that would take place over the ribs of the patient and beneath the patient's skin. A canister 12 is implanted near the left axilla, with lateral, anterior, or posterior positions being possible. A lead 14 couples the canister 12 to electrodes 16, 18 and 20, which are illustrated as implanted along the sternum of the patient, typically to the left or right thereof. The system in FIG. 1 may include an external programmer 22 configured for communication with the implant 12.

The system in FIG. 2 is a transvenous system, illustratively shown relative to the heart 30 again with the patient's ribs omitted for clarity. The canister 32 is in a high pectoral position, with the lead 34 accessing the vasculature and entering the heart. The lead 34 may include a superior vena cava coil electrode 36, a right ventricular coil electrode 38, and one or two ventricular sense/pace electrodes 40, 42. Again a programmer is shown at 44 and configured for communication with the implanted system. The system may further include a left ventricular lead (not shown).

Communication for either of the systems in FIG. 1 or 2 may be inductive, RF, direct (that is, using the patient's own tissue as a communication medium), or via any other suitable medium of communication. Such communication can be useful to configure the implanted system for sensing, therapy or other feature, to load new software or firmware for the implanted system, and to retrieve information about system operation such as device status, therapy history, diagnostic data (both device and patient related), or other suitable data. The programmers may contain such circuitry as is needed to provide processing, memory, display, telemetry/RF communications and the like for these noted purposes.

The canisters in FIGS. 1 and 2 will typically contain operational circuitry for the implantable system. The operational circuitry may include a controller and any suitable analog and/or digital circuits needed for signal processing, memory storage and generation of high-power electrical, low-power electrical and/or non-electrical outputs. For example, an analog to digital converter (ADC) can be a direct conversion ADC, a successive approximation ADC, a ramp comparing ADC, a Wilkinson ADC, an integrating, dual slope or multi-slope ADC, a pipeline ADC, or a sigma-delta ADC. Other ADC types, a modifications and/or hybrids of any of these types, may instead be used as those skilled in the art will appreciate.

The operational circuitry may be coupled to suitable battery technology for an implantable device, with any of numerous examples well known in the art, and may use various capacitor technologies to assist in the short term build-up and/or storage of energy for defibrillation or other high output purposes. The leads and external shell for the canisters can be manufactured with various materials suitable for implantation, such as those widely known, along with coatings for such materials, throughout the art. For example, the canisters can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. The electrodes can be formed of suitable materials as well, such as silver, gold, titanium or stainless steel such as MP35N stainless steel alloy, or other materials.

The location of system implant may vary. For example, the system shown in FIG. 1 is a subcutaneous-only system located on the anterior and lateral chest between the skin and ribcage of the patient. Other subcutaneous only systems (including systems without a lead 14, with multiple leads 14, or an array in place of lead 14) may be used with other anterior only placements and/or anterior-posterior, posterior only, left-right, etc. locations, including, for example, locations noted in U.S. Pat. Nos. 6,647,292, 6,721,597, 7,149,575, 7,194,302, each of which is incorporated herein by reference, and other locations as well. Subcutaneous placement can include any location between the skin and ribcage, including sub-muscular.

Illustrative transvenous systems, in addition to that of FIG. 2, include single chamber, dual chamber and biventricular systems. A fully intravenous system has also been proposed. Additional or other coatings or materials than those noted above may be used, particularly for epicardial, transvenous or intravenous systems, leads and canisters. Systems may further include an implantable "seed" that can attach directly to the myocardium without a lead at all. Some systems may combine an implantable, intracardiac seed with a subcutaneous-only defibrillator, with the seed and defibrillator enabled for two-way communication such as commanded therapy delivery and/or conveyance of sensed data.

Various alternatives and details for these designs, materials and implantation approaches are known to those skilled in the art. Commercially available systems in which the above methods can be performed or which may be configured to perform such methods are known including the Boston Scientific Teligen™ ICD and S-ICD™ System, Medtronic Concerto™ and Virtuoso™ systems, and St. Jude Medical Promote™ RF and Current™ RF systems. Such platforms include numerous examples and alternatives for the various system elements.

As shown and described there are various ways in which an implantable cardiac rhythm management device or system may be implemented with respect to the current invention. In several examples, the methods and devices that are focused upon in the present invention include the ability to capture and analyze a far-field cardiac signal. Some examples of far-field signals include a signal captured between two subcutaneously placed electrodes, or between a canister electrode and an intracardiac electrode. Near field signals and/or signals generated as a combination of near and far field signals may be assessed in other alternatives.

Figure 3:
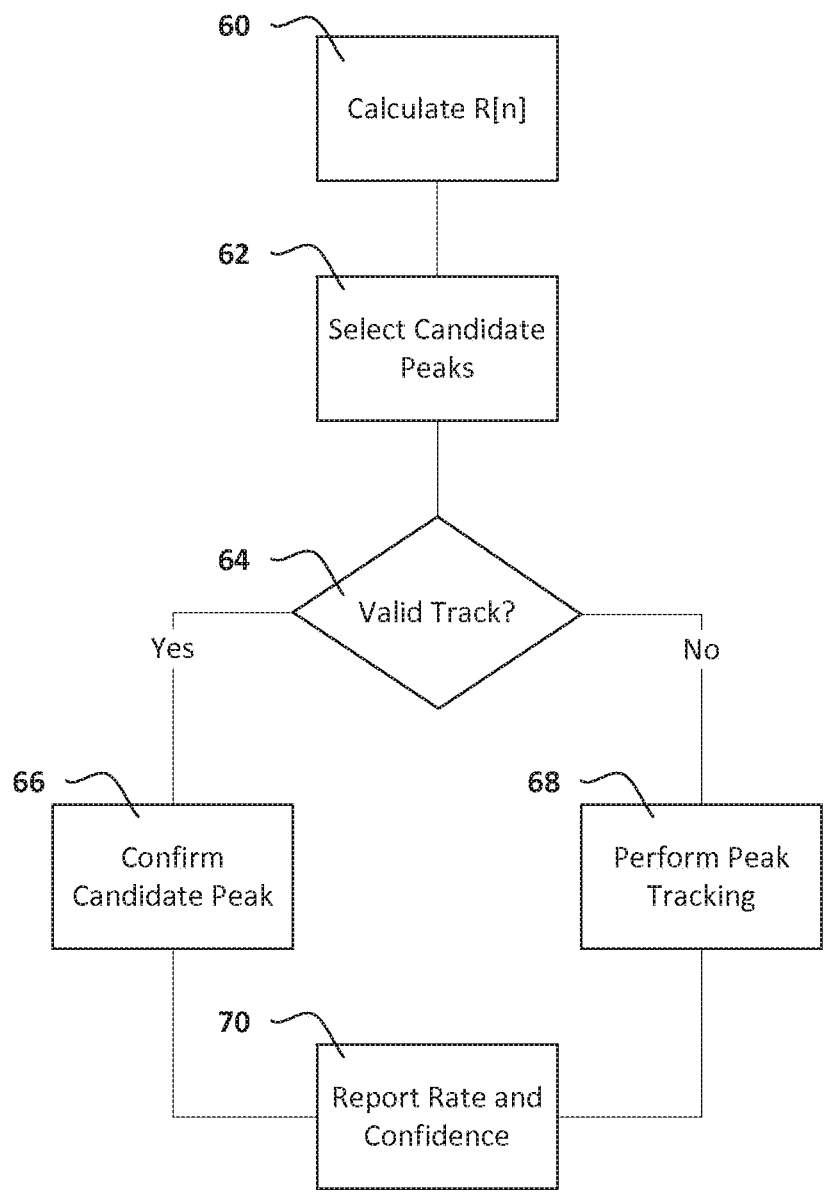
FIG. 3 shows an overall method for generating a cardiac rate estimate.
Figure 4:
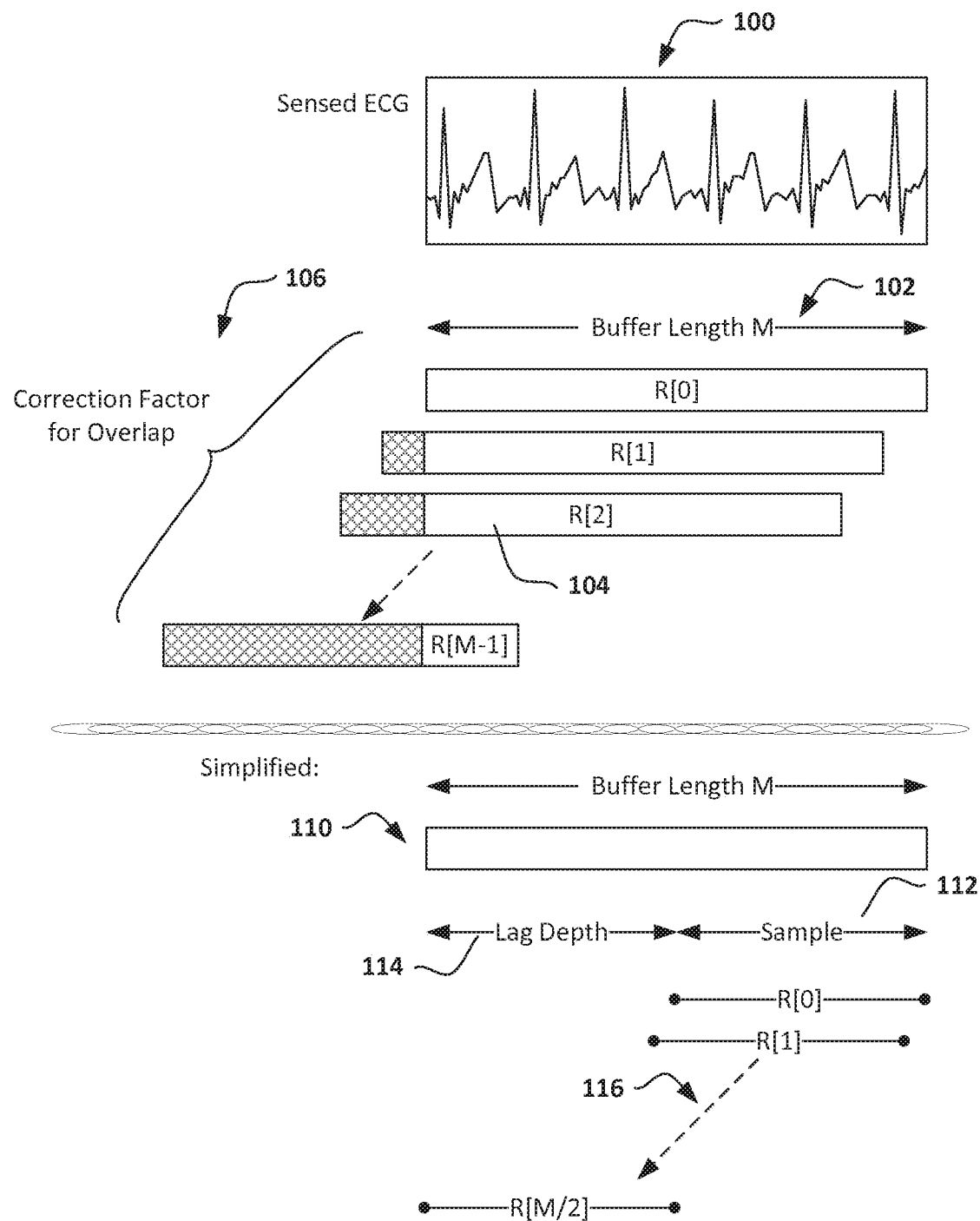
FIGS. 4-5 illustrate the analysis of data using a self-correlation function and differentiate such analysis from ACF.
Figure 5:
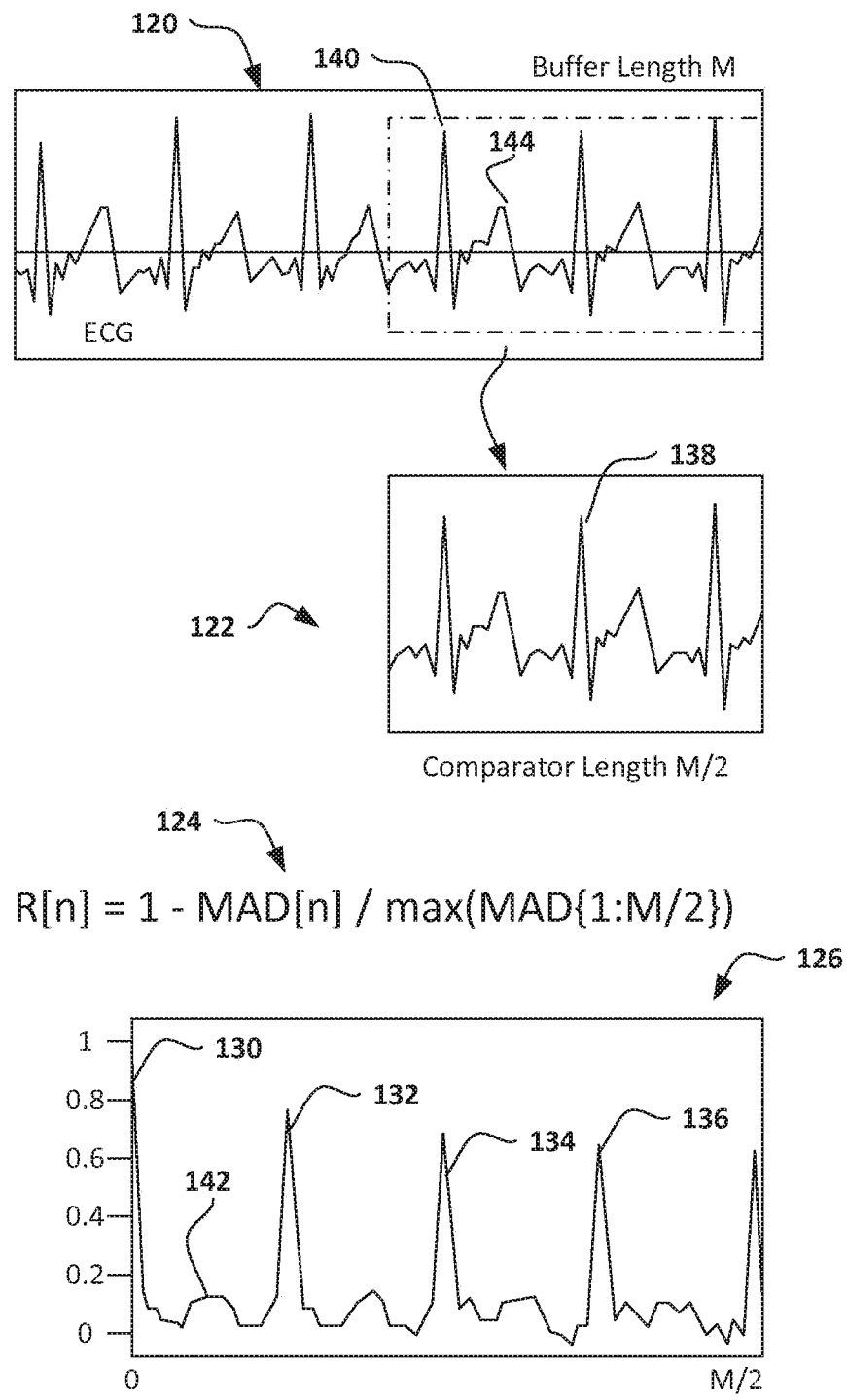

FIG. 3 shows an overall method for generating a cardiac rate estimate. A function "R[n]" is calculated. The function, R, may be, for example, a self-correlation function as illustrated in FIGS. 4-5, below. The function R represents a series of comparisons performed by calculating a relatively large number (50 or more) comparisons between a comparator that is a portion of a signal, and the overall signal itself, where the comparisons are performed by repeatedly shifting the comparator relative to the overall signal.

Figure 10:
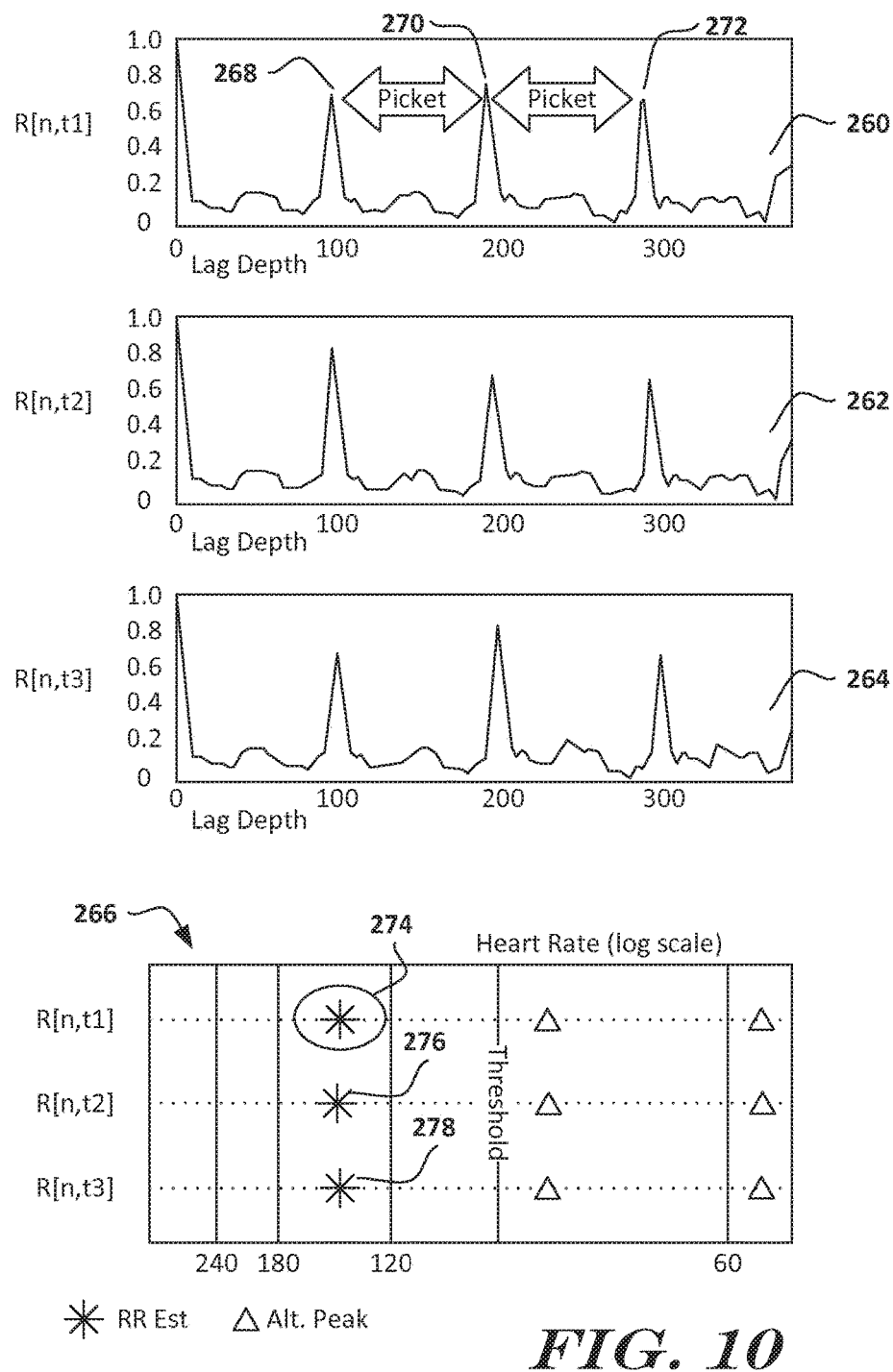
FIGS. 10-15 demonstrate several cardiac rate tracking steps using hypothetical examples.

R is discussed herein as a discrete function, rather than as a continuous function; in other examples, R may be a continuous function. In an example, R[n] may be a function that can be called periodically or it may be generated on a continuing basis. Briefly referring to FIG. 5, an illustrative R[n] as calculated at a selected point in time is shown at 140, based on a scrolling comparison of a comparator 122 to a buffer 120, the buffer 120 having length M and comparator a length M/2, providing R[n] a length of M/2. One could think of R[n,t], where n has values representing an individual calculation of R at a time t. For example, FIG. 10 shows three "R" functions—at each of t1, t2 and t3, R was calculated for n=0 to 400.

Figure 6:
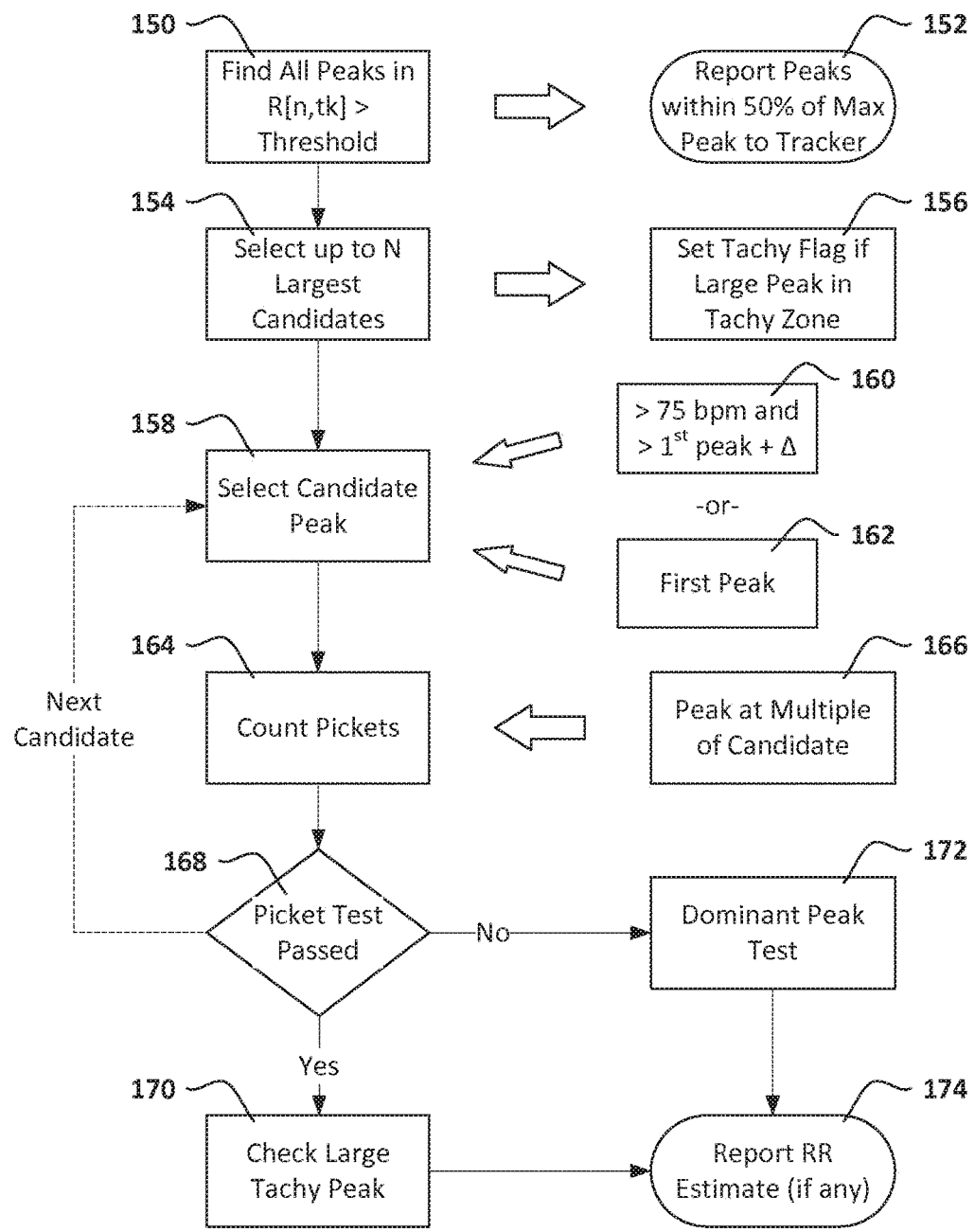
FIGS. 6-7 illustrate the analysis of R[n] peaks to identify candidate cardiac rates and a cardiac rate estimate.
Figure 7:
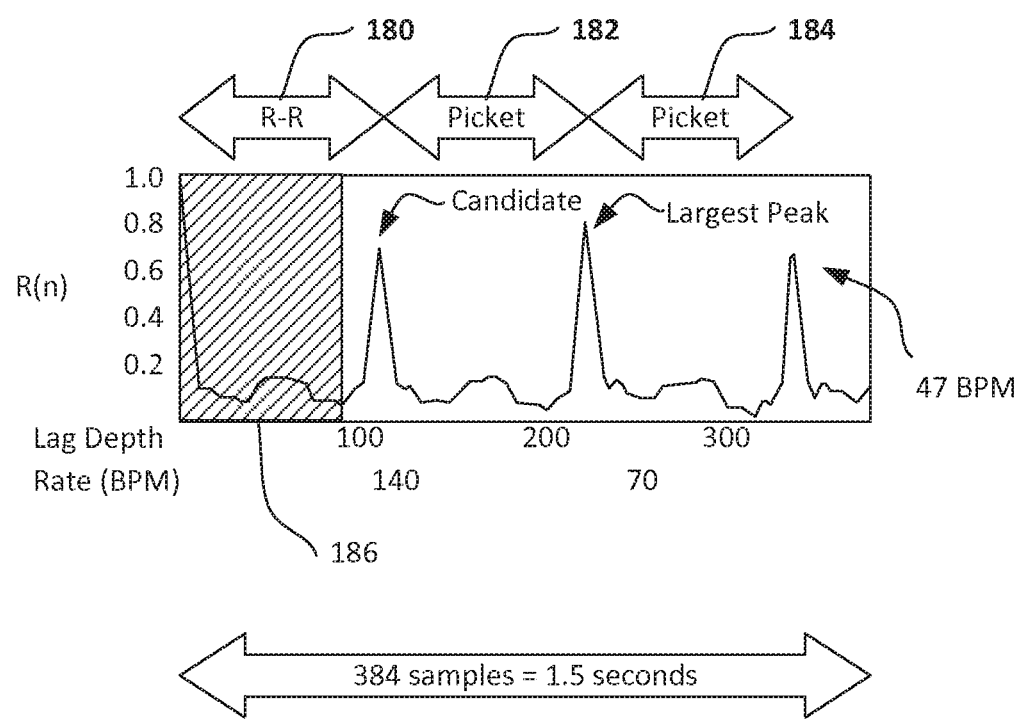

Using R[n] as calculated from step 60, a number of candidate peaks are identified at 62. FIGS. 6-7 provide examples of the identification of candidate peaks. Candidate peaks can be understood as representing a potential "rate" of cardiac events. A high match, as represented by a peak in R[n], suggests alignment of the cyclic electrical waveforms associated with a heart beat. For example, if a peak of R[n] occurs at n=90, and the sampling rate is 256 Hz, then the time between R[0] and the peak would be 90/256=352 ms. For this example, shifting the comparator back in time by 352 ms generates a relatively higher match between the comparator and the original signal. The 352 ms can be referred to as the lag depth, and if it truly is the interval between successive R-waves, it would correspond to 171 beats per minute (bpm).

Figure 8A:
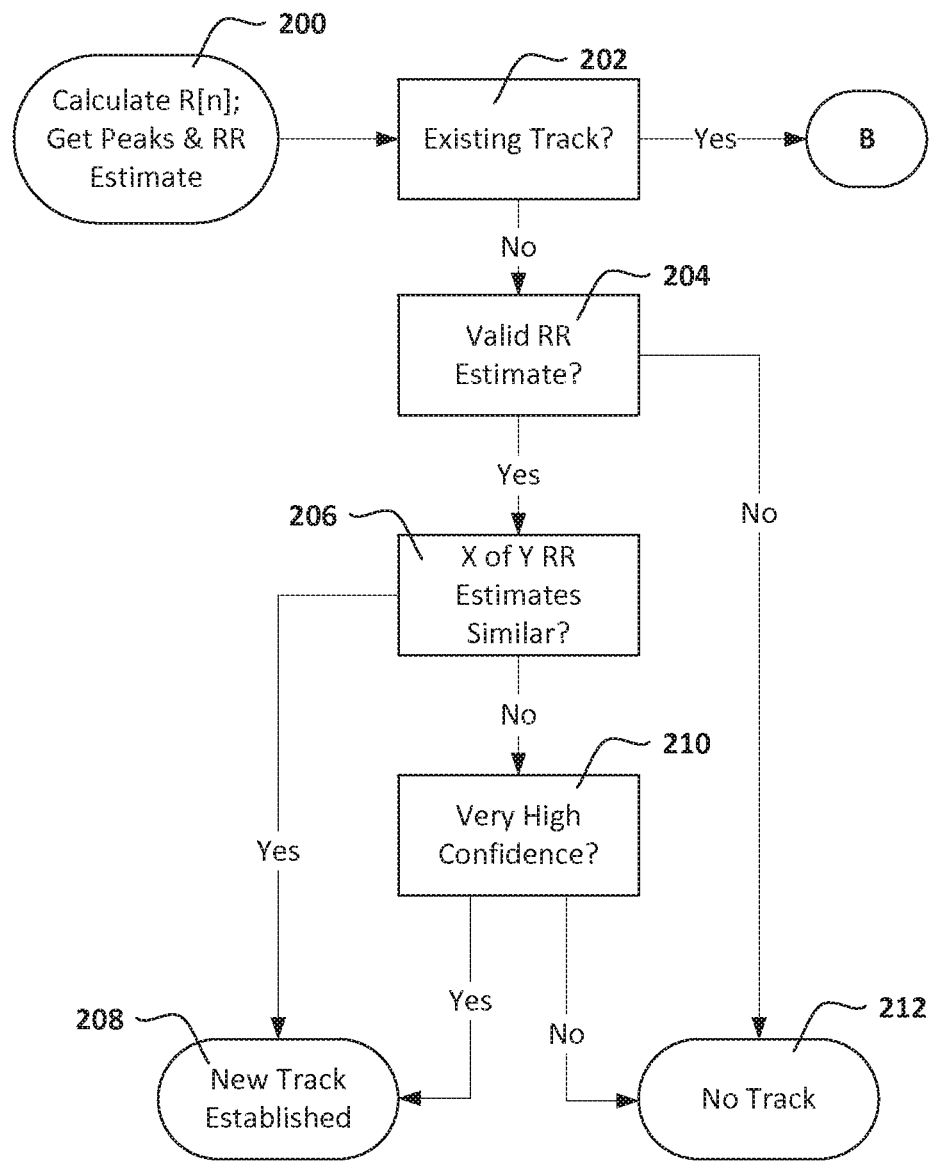
FIGS. 8A-8B illustrate one method of tracking cardiac rate.
Figure 8B:
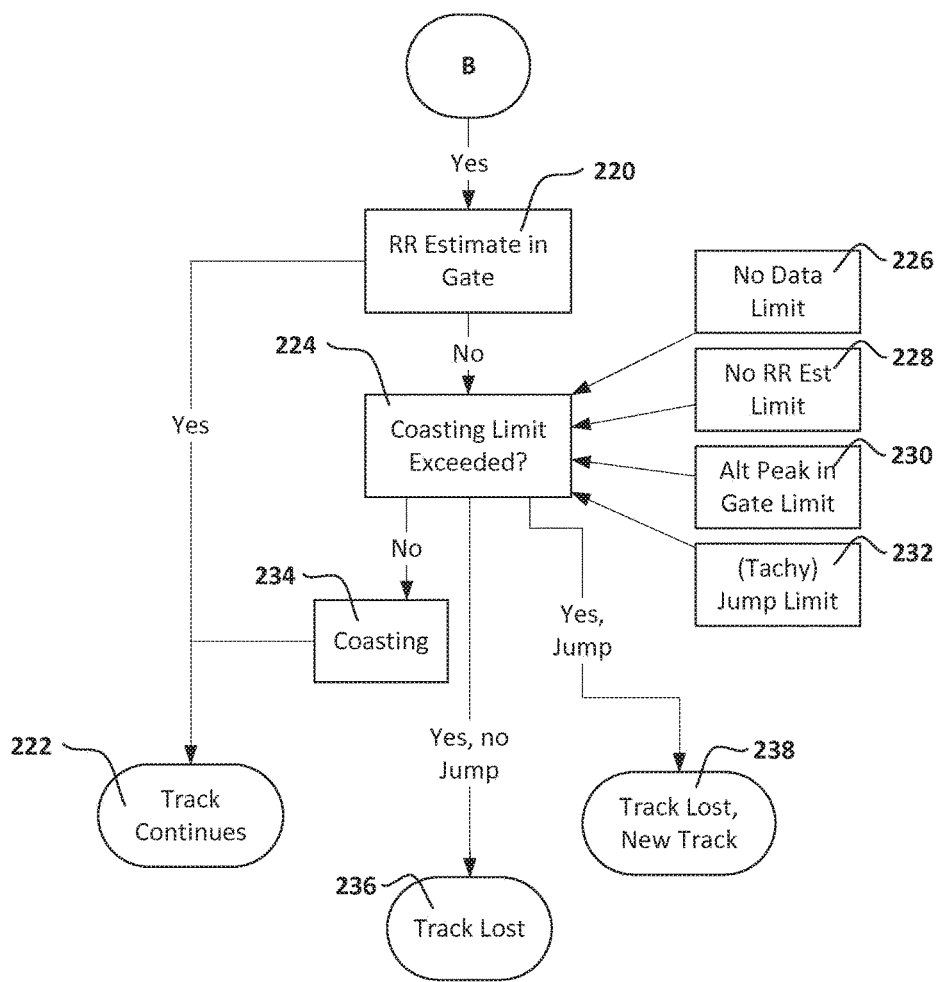
Figure 9:
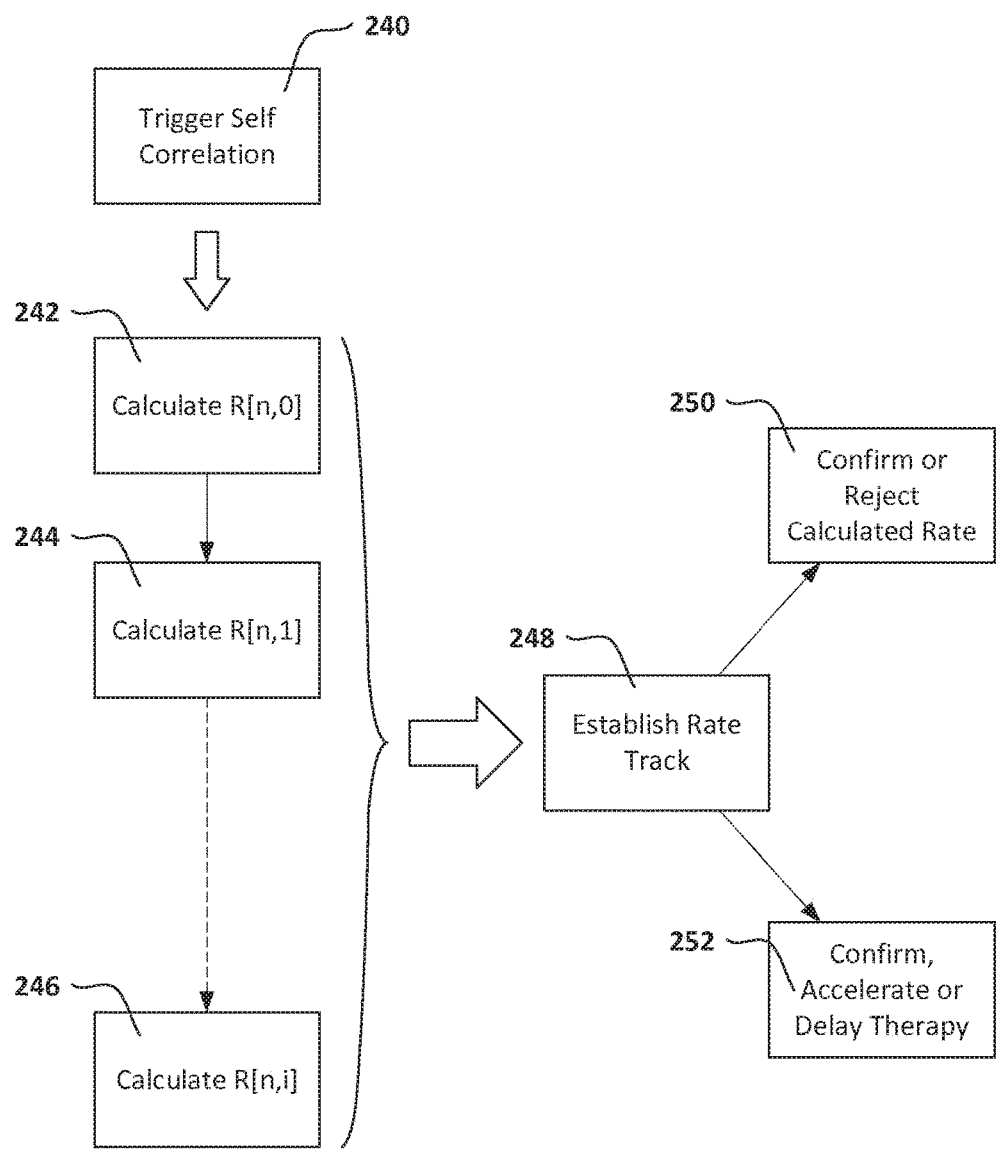
FIG. 9 illustrates tracking of cardiac rate over time.

Next the method determines whether a valid track exists, at 64. Tracking is the process of monitoring the outputs of the R[n] calculation and peaks therefrom to determine whether a high-confidence cardiac rate can be reported. FIGS. 8A-8B show an illustrative method of rate tracking. FIG. 9 shows another approach to rate tracking.

If a track already exists, the method includes determining whether to confirm one of the candidate peaks, as shown at 66. If no track exists, then peak tracking is performed as shown at 68 to determine whether a new valid track can be declared. Next, following either 66 or 68, the method concludes the iteration shown by reporting a rate and confidence.

In some instances, no high confidence rate will be reported. For example, an atrial arrhythmia that is conducted to the ventricles may be characterized by unstable periods between ventricular depolarizations. As a result, the measured ventricular rate can be highly variable. When the ventricular rate is highly variable, R[n] may produce only relatively low peaks, or may not produce consistently similar peaks during iterative calculations. As a result, the output rate from the entire procedure may either be missing or may be reported with only low confidence at block 70. FIGS. 10-13 illustrate an example showing several iterations of the method of FIG. 3.

In an example, the output rate and confidence can be used to confirm or call into question the cardiac rate as calculated using a more conventional process. For example, a device may use a default beat detection scheme in which the received cardiac signal, following amplification and filtering, is compared to a detection threshold. Some illustrative beat detection approaches are shown in, for example, U.S. Pat. Nos. 8,565,878 and 5,709,215, the disclosures of which are incorporated herein by reference. Crossings of the detection threshold can then be presumed to represent beats or R-waves, and various known methods can be used to identify and eliminate detection threshold crossings that are caused by noise or overdetections. See, for example, U.S. Pat. Nos. 7,248,921, 8,160,686, 8,160,687, 8,265,737, and 8,744,555, the disclosures of which are incorporated herein by reference.

The remaining detected beats or R-waves, and intervals therebetween, can be used to calculate rate. The present invention, in some embodiments, is used to double-check the rate calculated using such methods. Such double checking can be called as needed or provided on a continuing basis. For example, a double check may be performed to confirm rate prior to therapy delivery, or prior to preparations for therapy delivery. In some embodiments, the present invention may provide a rate estimate which can override the rate as calculated using other methods such as beat detection.

In another example, a double check may be performed to confirm accurate event detection as a way of verifying a sensing configuration where, if the sensing configuration is not verified, a sensing vector may be changed. In other embodiments, elements of the present invention can be used to provide rate calculation by default, or may be the sole source of rate calculations.

FIGS. 4-5 illustrate analysis of data using a self-correlation function and differentiate such analysis from ACF. Certain additional options and examples can be found in U.S. Provisional Patent Application No. 62/038,440, titled CALCULATION OF SELF-CORRELATION IN AN IMPLANTABLE CARDIAC DEVICE.

FIG. 4 shows a sensed ECG signal at 100. The signal can be treated as a buffer of length M, as shown at 102. The calculation of R[1], R[2] . . . R[M−1] is illustrated at 104. Each calculation of R[n] is performed, in ordinary ACF, by multiplying (via dot product) a portion of the buffer and a portion of the comparator, with the comparator shifted in time relative to the buffer. The comparator itself is simply a copy of the original buffer. Because of the shifting in time, a correction factor is needed as shown at 106, since the dot product is calculated using fewer and fewer data points as the overlap is reduced in size with each successive calculation of R[n]. The shifting of the comparator may be referred to as a lag depth.

A first simplification is to replace the multiplication to calculate a dot product with subtraction. The absolute value of the subtraction result yields a Minimum Absolute Difference (MAD). Swapping the dot product out and instead using MAD will reduce the number of required calculations by an order of magnitude or more, with minimal reduction in accuracy.

Next, to eliminate the correction factor for overlap 106, the buffer 110, having length M, is divided in half, to provide a sample portion M/2 and an available lag depth 114. Then the iterative comparisons identify the area of difference between the sample 112 and the buffer 110. As shown at 116, the result is M/2 total comparisons from a lag depth of zero to a lag depth of M/2.

An additional simplification may be performed in some embodiments by compressing the input data. For example, a system may perform analog-to-digital conversion of the cardiac signal at a rate of 256 Hz. The calculation of R[n] maybe performed on a limited or compressed version of the original signal, reducing the number of calculations again (though at the cost of calculations needed for downsampling, which may already be performed to facilitate data storage).

Turning to FIG. 5, an example calculation of R[n] at a particular point in time is shown. The ECG is shown at 120, as stored by a buffer having a length M. The comparator for the self-correlation is shown at 122, and comprises the half of the buffer 120 having the most recently detected samples. Preferably, the length of M is enough such that at least 2 beats will fit within the comparator during benign rate (such as 60 bpm). Thus in an illustrative example, the buffer 120 has a length of about 4 seconds and the comparator 122 has a length of about 2 seconds. Another example has a buffer 120 length of about 2 seconds and a comparator 122 with a length of about 1 second. Other sizes may be used. In some examples, the invention is characterized by having a buffer large enough to ensure at least two cardiac cycles occurring at a defined lowest needed rate would be captured, where the lowest needed rate may be in the range of 60-120 bpm. In further illustrations, the buffer length could be from 1.5 to 6 seconds and the comparator length is between 750 milliseconds and 3 seconds. In the examples shown herein, the comparator is half the length of the buffer; in other examples, the comparator may be between one-tenth to one-half of the overall buffer length.

As shown at 124, an MAD function is applied in this example, and is then normalized using the maximum of the MAD across all of the comparisons made for a particular iteration of R[n]. This yields a result that is graphed at 126. The resulting graph includes a peak at 130, which corresponds to the zero lag depth calculation, during which the MAD would be zero, giving an output of 1. The next peaks 132, 134 and 136 each correspond to points in time where the MAD is calculated while the R-wave peaks in the comparator are aligned with a set of R-wave peaks from the buffer. For example, if peak 138 of the comparator is aligned with peak 140 of the buffer, this would also align the adjacent peaks if the R-wave intervals are similar, giving a small absolute difference at that particular alignment.

Other peak alignments between the comparator 122 and the buffer 120 may generate lesser peaks in R[n]. For example, peak 142 occurs when peak 138 of the comparator is aligned with the T-wave at 144. This positioning creates a smaller MAD output which, once normalized using formula 124, would generate a noticeable but small peak in R[n].

The R[n] function may be calculated periodically. In one example, because the buffer and comparator take up fairly large blocks of time, such as more than one second or even two seconds, there is no need to continuously recalculate R[n]. For example, the period between recalculations of R[n] may be approximately the duration of the comparator, or, in another example, approximately half the duration of the comparator. For example, if the comparator length is 2 seconds, the buffer may be 4 seconds long and the calculation of R[n] could be performed at one second intervals. Thus, every second, the buffer would be updated and the comparator reformed, and the sequence of comparison and time shifting would be repeated. FIG. 10, for example, shows repeated calculation of R[n] at t1, t2, and t3, hence, R[n,t1], R[n,t2], and R[n,t3] are shown at 200 of that figure.

The illustrative examples in the various Figures herein suggest the use of an asynchronous calculation of R[n]. These are asynchronous insofar as the calculation is not linked or synchronized to a beat detection. Other embodiments may instead use a beat synchronous update or recalculation of R[n]. A hybrid embodiment may update synchronously to take advantage of microprocessor/microcontroller wakeup caused by beat detection, but may limit calculation of R[n] to occur no more frequently than some desired metric. For example, calculation of R[n] may be beat synchronized at intervals of no less than one second.

The optional simplifications in FIGS. 4-5 are provided for explanation and illustrative purposes. However, these simplifications can be omitted in some embodiments, as the peak selection and/or tracking examples shown below are not contingent on any particular type of calculation for R[n] unless otherwise stated.

FIGS. 6-7 illustrate the analysis of R[n] peaks to identify candidate cardiac rates and a cardiac rate estimate. FIG. 6 shows the operation in a flow diagram, while FIG. 7 provides a graphic example. Further explanation, examples and optional elements are shown in U.S. Provisional Patent Application No. 62/038,438, titled PEAK SELECTION

FOR SELF-CORRELATION ANALYSIS OF CARDIAC RATE IN AN IMPLANTABLE MEDICAL DEVICE.

In FIG. 6, beginning at block 150, the method starts with the identification of any peaks within R[n,tk]. In this example, peaks that are within 50% of the largest peak and that meet some minimum size criteria are reported forward to a peak tracker, as indicated at 152. Tracking may be performed as shown below in FIGS. 8A-8B and 9, for example.

A set of largest candidates are then selected, as indicated at 154. In an illustrative example, a threshold may be set within the scaled calculation of R. For example, using the formula 124 in FIG. 5, the threshold for candidate peaks may be set at R=0.3, such that in order to be considered a candidate, a peak must be larger than 0.3 times the largest peak. The largest peak will always occur at R[0], as that is when the comparator and buffer are perfectly aligned and thus R[0]=1. Any subsequent peak greater than 0.3 may be a candidate peak. In an example, up to five of the largest peaks greater than 0.3 (excluding the peak at R[0]) are treated as candidates.

As shown at 156, if any of the largest candidates have a lag depth which would place the candidate in the "tachy zone", a tachy flag is set. A candidate peak is in the "tachy zone" if the lag depth of the peak is relatively small. This may be identified by asking whether there is a peak at R[nt] where nt is less than a tachy threshold. For example, if the tachy zone flag is to be set for candidate peaks suggesting a rate above 160 bpm, and the sampling rate is 256 Hz, then a peak at n<96 is in the tachy zone, since the peak occurs with a lag depth of less than 375 ms equating to a rate above 160 bpm. The tachy flag, if set, indicates that the analysis suggests possible tachycardia, regardless the rate it ultimately concludes is most likely correct.

Next, a first candidate peak is selected as shown at 158. Either of two rules for finding the candidate peak can apply: a peak having a lag depth that allows a rate to be found that is greater than 75 bpm and which is larger than the first-in-time peak by a chosen limit, delta, can be chosen, as shown at 160 or, otherwise, the first-in-time peak of the candidate peaks is chosen, as shown at 162. The first-in-time peak is the candidate peak having the least lag depth. The first rule, at 160, allows a peak which is significantly larger than the first-in-time candidate peak to be selected, as long as it is above a rate threshold.

In the illustrative example, the combination of 160 and 162 ensure that peaks associated with higher rates will be analyzed first and, to this extent, biases the method to seek out higher rate candidates. A bias toward higher rates may be desirable to minimize the risk of heart rate underestimation in the presence of a tachyarrhythmia.

Next, the candidate peak is analyzed by looking for and counting "pickets", as shown at 164. The pickets are peaks at multiples of the lag depth of the candidate peak. FIG. 7 shows an example of pickets. A first peak is found at a lag depth of 110 samples (corresponding to 140 bpm sampled at 256 Hz). This lag depth gives an R-R interval as shown at 180. Two pickets can be identified by observing additional peaks at lag depths of 220 samples and 330 samples, which are multiples of the lag depth of the candidate. The pickets at 182 and 184 provide confirmation that the 140 bpm rate is likely the correct cardiac rate.

The counting of pickets can include an allowance for some variation in peak spacing. For example, the picket peaks should be equally spaced, within a maximum tolerance. The tolerance can be defined as a function of the calculated heart rate, or may be set in terms of milliseconds or samples (n). For example, if a first peak is at a lag of 80 samples (313 milliseconds at 256 Hz), a picket would be expected to appear between 75 and 85 samples away (293 milliseconds to 332 milliseconds). A narrower or wider tolerance may be defined in other examples.

It should be noted in this example that the largest peak is not the first selected candidate peak. There are two reasons why this is so: first, the largest peak is not sufficiently large relative to the candidate peak to meet rule 160. In an example, to select a peak other than the first peak as a candidate, the later peak needed to be at least 30% larger than the candidate (making delta relative), which is not the case here. In another example, delta may be a fixed value, such as 0.2 using the MAD formula 124 from FIG. 5.

Second, the largest peak is at a lag depth corresponding to a rate of 70 bpm, again not meeting rule 160. In the example, to select a peak other than the first peak as a candidate, the later peak needed to be at a lag depth corresponding to a rate greater than 75 bpm. Other thresholds may be chosen. The picket determination may require that the peaks used to establish subsequent pickets be among the largest N peaks or that each peak be larger than a predetermined threshold, such as a peak above 0.35 or 0.50 using the formula at 124 in FIG. 5.

Both of rules 160, 162 can be modified in other examples, and some examples may omit one or the other.

For illustrative purposes, FIG. 7 also illustrates a tachy zone 186. The tachy zone, in this example, covers a lag depth from zero to about ninety. This corresponds to an offset of up to ninety samples. In the illustration shown, 384 samples equate to 1.5 seconds, meaning a 4 ms sampling period. Ninety samples would correspond an RR Estimated Interval of 360 ms, equating to 167 bpm. As noted above, other settings for the tachy zone may be used.

Returning now to FIG. 6, the method proceeds by determining whether the picket test passed, as shown at 168. In an example, the picket test passes if there are at least two pickets identified relative to the candidate peak.

If the picket test is passed, the method does a final check for any large peak in the tachy zone, as shown at 170. In some, limited instances, a large number of peaks may be reported during a chaotic tachy event. In such a case, the decision to select only "N" largest candidate peaks at block 154 could fail to choose as a candidate a peak in the tachy zone. Therefore the test at 170 looks for any peak in the tachy zone which is within 30% of the size of the largest peak, but which did not get identified as a candidate.

If a large tachy zone peak is identified at 170, this peak is subjected to a picket test as well. If the peak chosen at 170 has pickets such that it passes the picket test, then the large tachy zone peak from block 170 is reported as the RR estimate at 174. Otherwise, as noted at 156, the tachy zone flag is set and the candidate peak that did pass the picket test at 168 will be reported as the RR estimate at 174.

In some examples, all candidates may be checked until one is found which passes the picket test and, if no picket test passes can be found for any of the candidate peaks, the method proceeds to block 172. Alternatively, only the first selected candidate peaks is subject to the picket test at 168, and, upon failing the picket test once, the method goes to block 172.

Upon reaching block 172, a dominant peak test is applied. The dominant peak test determines whether there is a peak that is 30% larger than all other peaks in R[n] (excluding the peak at n=0). If so, then that dominant peak is identified as the RR estimate.

The dominant peak test 172 may also be limited to passing when the identified dominant peak is at a lag depth corresponding to a rate below a preset threshold, such as 60, 75 or 90 bpm. The rate limit may be included in block 172 as an acknowledgment that there may be no pickets in the analyzed data for a low rate peak. This is so because the time span of the R[n] calculation may not be sufficient to produce a picket pattern for all heart rates, particularly lower heart rates with longer beat intervals.

For example, using a buffer of 3 seconds and comparator of 1.5 seconds length, the first picket for a peak at a lag depth of 800 milliseconds (75 bpm) would be at 1.6 seconds. Such a picket could not be identified given the buffer/comparator sizes, as the greatest lag depth is only 1.5 seconds given the 3 second/1.5 seconds buffer/comparator sizes. On the other hand, a dominant peak at a smaller lag depth, such as 500 milliseconds (120 bpm) would be expected to have two pickets in this scenario, and, absent any pickets, would not be treated as a highly likely RR estimate as there would appear to be less periodicity than would ordinarily be associated with a confident RR estimate.

If an RR estimate is calculated via one of the three possible avenues—candidate peak passing the picket test (158-164-168), a large tachy peak (170) or the dominant peak test (172), the RR estimate can be reported out. A confidence grade can also be applied. In an example, three grades are available:

HIGH confidence if either
    Rate>TachyThreshold with 3 pickets and R>HCThreshold, or
    Rate<TachyThreshold with 2 pickets and R>HCThreshold;
MID confidence by default if no High or Low Confidence condition is met; and
LOW confidence if
    R<LCThreshold or
    1 or fewer pickets and Dominant Peak Test 172 not passed In this example, TachyThreshold can be set in a range calling for high rates, for example, over 150, 180 or 200 bpm. In some examples, TachyThreshold may be selected in light of the buffer and comparator size, in order to link to the quantity of pickets that could appear. The HCThreshold definition will be reliant on just how R is computed. In an example, given computation of R using the formula at 124 in FIG. 5, HCThreshold is set at 0.65. Likewise, LCThreshold will be defined in a manner closely tied to the computation of R. In an example also using formula 124 from FIG. 5, LCThrehsold is set to 0.35.

The confidence information may also be incorporated into the tracking steps shown in FIGS. 8A-8B. For example, switching from one track to another, or declaring a new track, may be accelerated in response to a high confidence rate, while such steps may be delayed for a low confidence rate.

Figure 16:
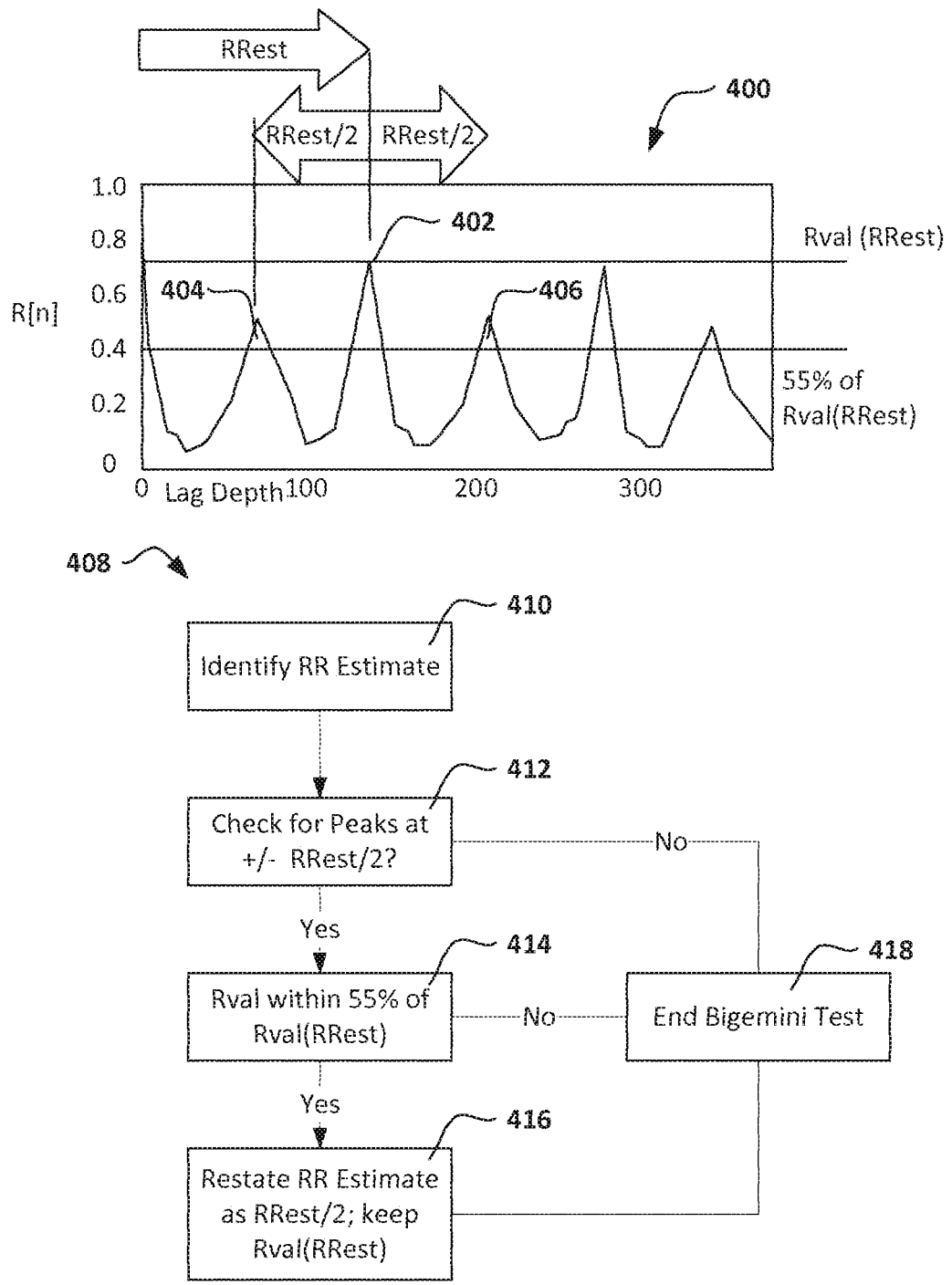
FIG. 16 illustrates an analysis to identify a bigemini rhythm and rate.
Figure 17:
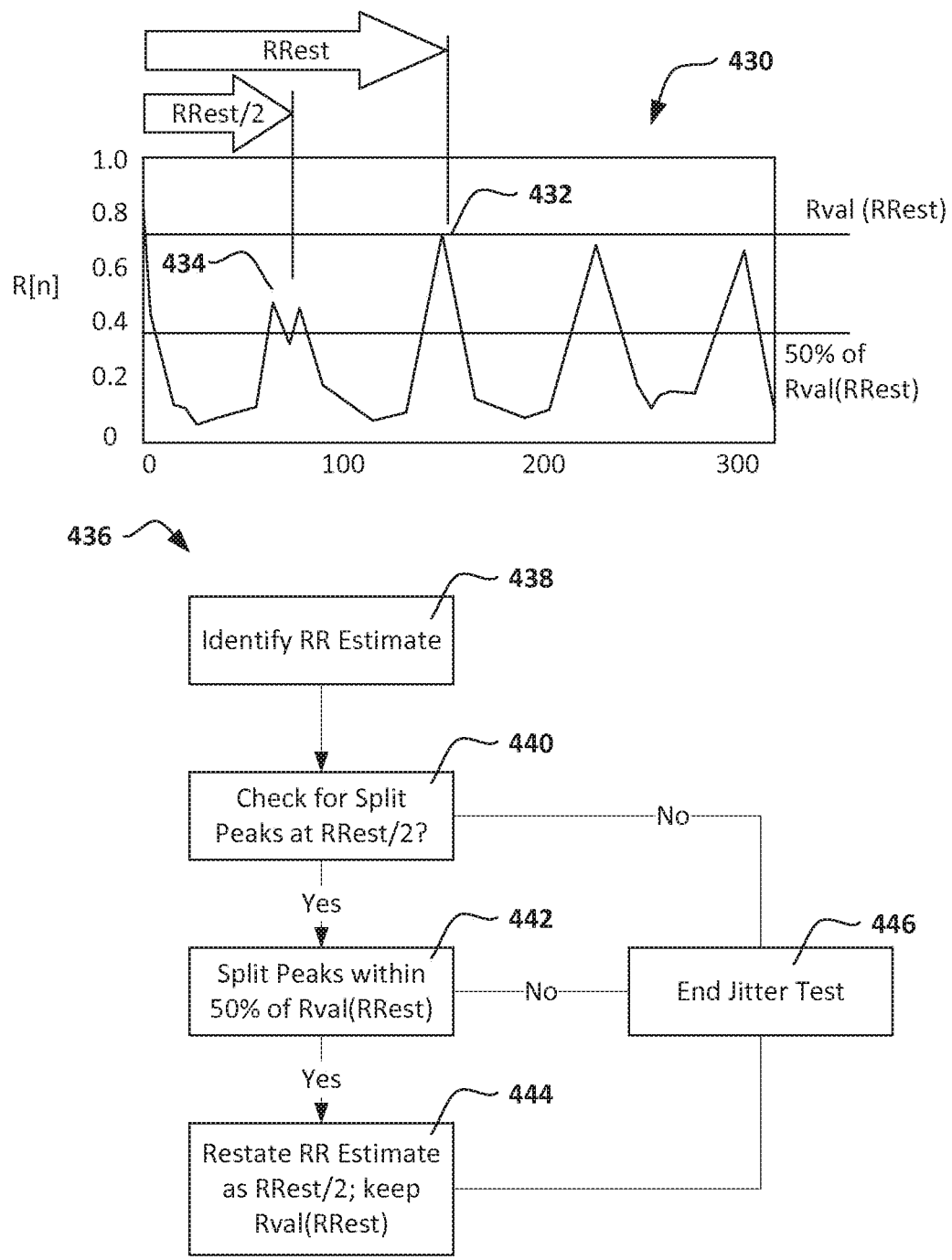
FIG. 17 illustrates an analysis to identify jitter.

In a Bigemini pattern, there are two alternating morphologies for ventricular depolarization or "R" waves. When a Bigemini pattern is analyzed using self-correlation, it can be difficult to determine whether the output reflects R-wave and T-wave peaks, which alternate and have different morphologies, or two R-waves having a Bigemini pattern. A particular ruleset is shown and demonstrated below in FIG. 16 to address a Bigemini pattern and reduce the likelihood of undercounting Bigemini and other regular-shape changing patterns. FIG. 17 addresses a test to check for jitter as well.

FIGS. 8A-8B illustrate one method of tracking cardiac rate. Starting at block 200 in FIG. 8A, any suitable manner of finding R[n], selecting a set of peaks and generating an RR Estimate are performed. The methods illustrated in FIGS. 4-7 provide various options for block 200. The tracking method begins by determining whether there is an existing or "active" track, as 202. If so, the method proceeds to B in FIG. 8B.

If there is no existing track, the method determines whether a valid RR Estimate has been generated, as shown at 204. If no valid RR Estimate can be had from the prior analysis, no new track will be declared, and the method terminates with no track at 212 and awaits a next iteration. If a valid RR Estimate was found, the method next determines whether X out of the last Y RR Estimates (or attempts) are similar, as shown at 206. For example, if 3 of the last 4 RR estimates are similar, the test at 206 would be met for an X/Y of 3/4. In one example, a 3 of 6 rule is applied at 206. If the test at block 206 is met, then a new track is established at 208.

If the test at 206 is not met, a new track may still be established on the basis of a single very high confidence rate calculation. The definition of very high confidence may vary. In one example, the HIGH/MID/LOW confidence rules applied above may be used, and any RR estimate that is calculated with HIGH confidence would be sufficient to meet the rule at 210. In another example, a separate threshold for the very high confidence rule at 210 may be set. In one embodiment, block 210 is met when R>0.85 in a system calculating R using the formula shown at 124 in FIG. 5. If the rule at 210 is met, a new track is established as shown at 208. Otherwise, no new track is set, as noted at 212.

Turning to FIG. 8B, a valid track exists, and it is determined whether the latest RR Estimate is within the Gate, as shown at 220. The Gate has a width, which can be defined in various ways. For example, the gate may be 40 milliseconds wide, or it may be 20 bpm wide. The Gate may be centered on a prior RR Estimate or average of 2-4 previous RR Estimates. In one illustration, the Gate is calculated by converting the most recent RR Estimate to bpm, and setting the upper and lower bound 10 bpm away. Thus, for example, if the most recent RR estimate is 400 ms, that converts to 150 bpm, and the Gate would be from 140 bpm to 160 bpm and an RR estimate between 429 ms and 375 milliseconds would be considered "in" the gate.

Gate width may also factor in rate variability. For example, the variability of a set of recent RR Estimates can be calculated by simply tracking how much change there is one from one estimate to the next. The Gate width may be increased if the rate appears to be highly variable in this example.

If the RR Estimate is within the Gate, the method declares the track continued at 222. The RR Estimate is also reported out.

If the RR Estimate is not within the Gate, then the Coasting rules are applied. Coasting takes place when a valid track has been identified/defined, but an iteration of the RR Estimate calculation fails to yield a result that meets the track definition. The use of Coasting allows the track to continue and passes over temporary disturbances such as noise or PVC, for example. Coasting avoids gaps in the output RR Estimate by holding the last known RR Estimate. Coasting can be particularly useful when a peak exists in R[n] but fails, for whatever reason, to otherwise pass the rigorous tests in the peak selector for identifying the a candidate peak as an RR estimate. Coasting is available to salvage the RR Estimate for such peaks, but only for a limited time.

In the illustrative example, Coasting is not allowed to continue indefinitely and a limit is applied, as shown at 224. If coasting is within its limits, the method continues via block 232 and continues on the track at 222. To limit coasting, various rules can be applied and each may have a different limit.

For example, as shown at 226, if no RR estimate or peaks are reported up from the calculation of R, there may be a first, "No Data" limit to the duration of coasting. In an example, the system will only allow a single iteration of "No Data" before declaring the track lost at 236. Such a "No Data" condition can occur, for example, if noise has interrupted sensing and none of the peaks in R[n] exceed a base threshold. A "No Data" condition can also take place if a very polymorphic arrhythmia onsets, such that R[n] simply fails to have any significant peaks.

Next, there is a coasting state in which no RR Estimate is produced, as shown at 228, with this state also requiring that there not be any of the reported peaks in the gate, as shown at 230. Thus, block 228 covers one set of circumstances in which rate estimate is lacking and the track is not being confirmed, while block 230 covers a state in which there is a lower confidence confirmation of the track, whether or not an out-of-track RR estimate has been identified.

A fourth form of coasting can take place as part of a transition or "jump" to an alternate track, as noted at 232. In this instance the existing track continues until either an alternate track condition is met by having a "new" track declared using a similar determination as in 206 or 210 of FIG. 8A.

As can be seen from blocks 226, 228, 230, 232, there are different inputs to the coasting state, each of which comes with somewhat varying confidence levels. For example, confidence in the underlying track or sensing reliability is low when no data is received 226, and not much better when there is no RR Estimate reported and none of the reported peaks fall within the gate 228. These two blocks 226, 228 may be combined for a single limit in the range of 1-3 iterations before the coasting limit is exceeded. Alternatively, block 226 may have a lower costing limit (1-2 iterations) while block 228 has an equal or higher limit (1-4 iterations), with a combined limit matching the higher limit (1-4).

The alternate peak in gate condition, at 230, is a much higher confidence condition, by suggesting that the track may still be valid, even if sensing a anomaly, such as noise, is present. This condition 230 may have a still higher coasting limit, in the range of 2-10 iterations or may be subject simply to an overall limit (in the range of 2-10 iterations) which would combine any coasting within any of 226, 228, 230 or 232.

Block 232, the Jump limit, is present to enable quick transition to a new track, without having to first wait for a declaration that the track is lost at 236 before assessing whether a new track exists. The Jump limit also prevents a shift to a new rate based on peaks that appear within an old, but no longer valid, track. When a coasting limit is met at 224 via the jump limit, the outcome follows a different path to 238. As a result, if the Jump limit is met, the method simply continues with a new track definition. To meet the Jump limit 232, in an illustrative example, the same rule as was applied at 206 may be applied to the new track. As noted at 232, the Jump limit may be applied just for high rate conditions, which are of greater concern generally than low rate conditions, using, for example, a limit in the range of 100-180 bpm, with 150 bpm being one example rate in particular.

The use of the Jump allows a quick transition to a higher rate RR Estimate, with a less stringent rule set when there is an existing track and a jump takes place. In the example, to declare a new track when no track has been identified would require a higher confidence in the new data than is required for the jump.

If the coasting limit is exceeded at 224, the track will be declared lost, as noted at 236. If the coasting limit is not exceeded, the coasting "state" can be recorded 234, with different coast states identified for each of the different coasting conditions 226, 228, 230, 232. While coasting, the track continues as shown at 222 until the next iteration is called.

FIG. 9 illustrates tracking of cardiac rate over time. There may be various triggers for performing self-correlation, as noted at 240. For example, self-correlation may be a default, continuing analysis called by an implantable system throughout the life of the system. Alternatively, self-correlation may be called in response to an identified potential condition necessitating treatment, such as an elevated rate condition. In one example, the cardiac rate may be calculated using conventional R-wave detection schemes (often by comparing the detected cardiac signal to a time varying threshold). If the identified rate crosses a threshold, the self-correlation methods may be initiated to confirm elevated rate. Thresholds may be set, for example, in the range of 100-180 bpm, or higher or lower, as desired.

In one example, a cardiac therapy system may use a number of intervals to detect (NID) approach or an X/Y filter to transition from unconcerned state into a therapy preparation and delivery state. For example, an X/Y filter may call for 18 out of 24 prior detected heart beats to be analyzed and considered treatable before therapy is delivered. For such a system, if X reaches a lower threshold, for example, 8/24, the self-correlation may be called to begin analyzing and confirming (or rejecting) calculated rates before the 18/24 boundary is reached. Similarly, if an NID approach is used, an NID threshold that is below a therapy boundary may be used to trigger the self-correlation analysis.

In another example, self-correlation may be called to periodically confirm sensing integrity by calculating a cardiac rate for comparison to other rate calculation methods/circuits. In some examples, the self-correlation shown in the present application may serve as the sole estimator of cardiac rate in an implantable device.

Once the analysis is triggered at 240, the self-correlation is performed at intervals, such that R[n,t] is calculated for each of t={0, 1, . . . i}, as shown at 242, 244, 246. From this series of calculations, a rate track is sought and, if possible, established as shown at 248. The analysis may confirm or reject a calculated rate, as shown at 250.

In addition, the analysis may be used to confirm, accelerate or delay therapy delivery, as noted at 252. Returning to an above example, if the self-correlation is called once the cardiac rate identified by conventional R-wave detection crosses a threshold, if self-correlation confirms an elevated heart rate requiring therapy, a therapy threshold may be lowered. For example, if a system uses an X/Y counter set to 18/24, the counter may be reduced to 12/16 if self-correlation confirms a very high rate prior to the X/Y counter condition being met. In another implementation, the self-correlation RR estimate can replace a conventionally calculated heart rate for a specified period of time, quantity of detected events, or until a next calculation of R[n] and analysis thereof is performed.

FIGS. 10-15 demonstrate several cardiac rate tracking steps using hypothetical examples. FIG. 10 illustrates the initiation of a rate tracking activity. The self-correlation function is calculated at each of times t1, t2 and t3, as shown at 260, 262 and 264. For purposes of understanding operation of this embodiment, a graph at 266 illustrates how the peaks of each R[n] calculation align with one another. Looking at R[n,t1], the graph at 260 illustrates that three peaks above the R=0.3 threshold were found, at lag depths of approximately 95, 190, and 285 samples. Using the method of FIG. 6, these three peaks 268, 270, 272 would be reported out of the peak analysis.

Next, again using the rules shown in FIG. 6, the first peak 268 from R[n,t1] is chosen as a candidate peak. Pickets would then be sought. As illustrated, there are two pickets identified for candidate peak 268, to the additional peaks at 270 and 272. Thus the method of FIG. 6 would confirm that peak 268 provides the RR estimate, while each of peaks 268, 270 and 272 would be reported to the tracking engine.

The RR Estimate from R[n,t1] is shown in graph 266 at 274; the other peaks from R[n,t1] are also shown as alternate peaks. Likewise, RR Estimates result from the analysis of the other two calculations at R[n,t2] and R[n,t3], as shown at 276 and 278. Here, no track has yet been declared. As a result, each of the RR Estimates may be deemed to yield a medium-confidence rate estimate, until a track can be declared.

Figure 11:
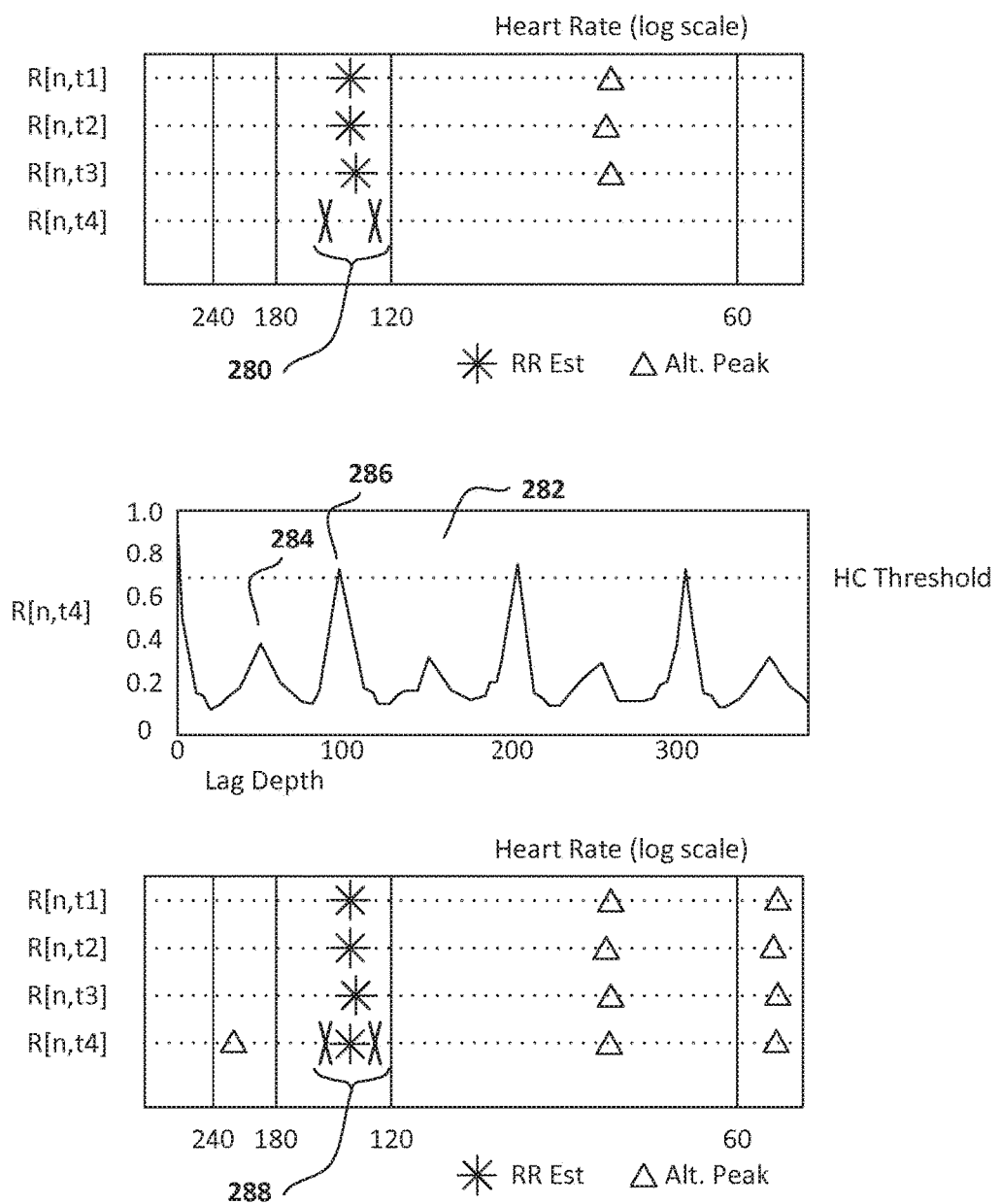

Turning to FIG. 11, the matching of the results for each of R[n,t1], R[n,t2] and R[n,t3] is sufficient to meet the track definition in FIG. 8B using a 3/6 rule. Therefore a track gate is shown at 280 for use in assessing the next iteration of the self-correlation, at R[n,t4]. The newly calculated R[n,t4] is shown graphically at 282. In R[n,t4], the peak associated with a T-wave comparison appears at 284 in addition to the much higher peak for the R-wave at 286. Again applying the rule set in FIG. 6, the first peak is at 284, and could be chosen if the rule at 162 in FIG. 6 controlled. However, the second peak at 286 is significantly larger than the first peak and appears at a lag depth that supports a rate greater than 75 bpm, meeting the rule at 160 in FIG. 6. Therefore peak 286 is selected for analysis, and is found as before to have two pickets (not shown) and is used to report out an RR Estimate. As shown at 288, the RR Estimate for R[n,t4] is within the gate.

It should also be noted that the peak 286 that is used for the RR Estimate exceeds an HC Threshold for high confidence. Therefore, the RR Estimate at 288 would then be used for rate reporting by the tracker, with high confidence.

Figure 12:
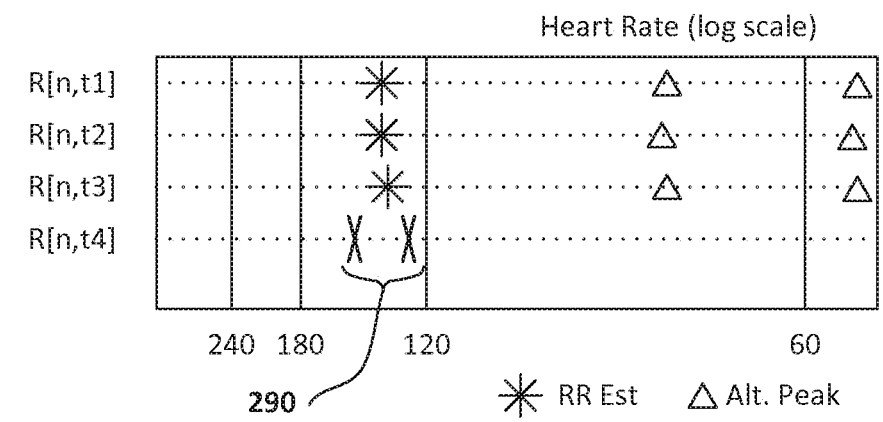
Figure 12:
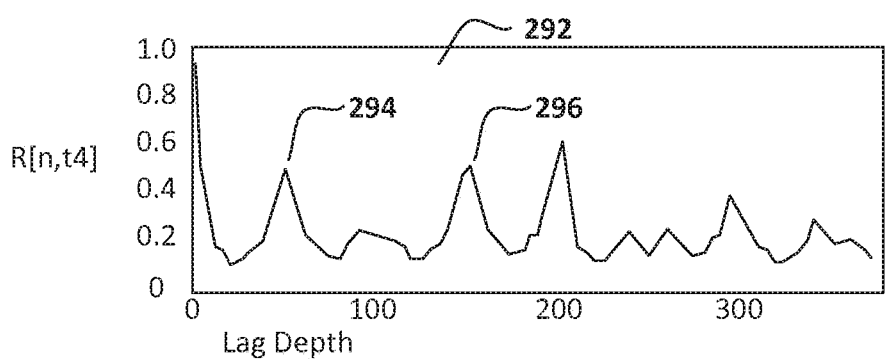
Figure 12:
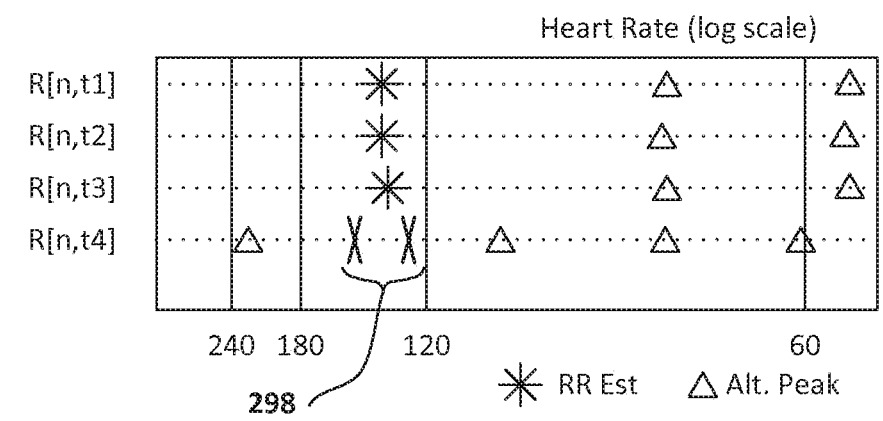

FIG. 12 presents a different scenario for the calculation of R[n,t4] after the track is established and gate is set at 290. Here, the output has changed dramatically from R[n,t3] to R[n,t4], as shown at 292. Using the rules of FIG. 6, the first peak 294 is chosen as a candidate peak, however, no pickets are found because the next significant peak, at 296, is too far away. There is also no dominant peak. As a result, no RR Estimate is calculated.

Looking at the updated overall graph, it can be seen that gate 298 is empty, without an RR Estimate or an alternate peak therein. As a result, for R[n,t4], the analysis is in a coasting state in FIG. 12. Because no RR Estimate could be calculated based on R[n,t4], a rate would not be reported to the Peak tracker. Because the track continues in a coasting state, an output rate estimate would be provided and, in an example, would be a value within the gate or could be the same as a previous output. Based on the empty gate at 298, the output rate estimate would be given a low confidence level.

Figure 13:
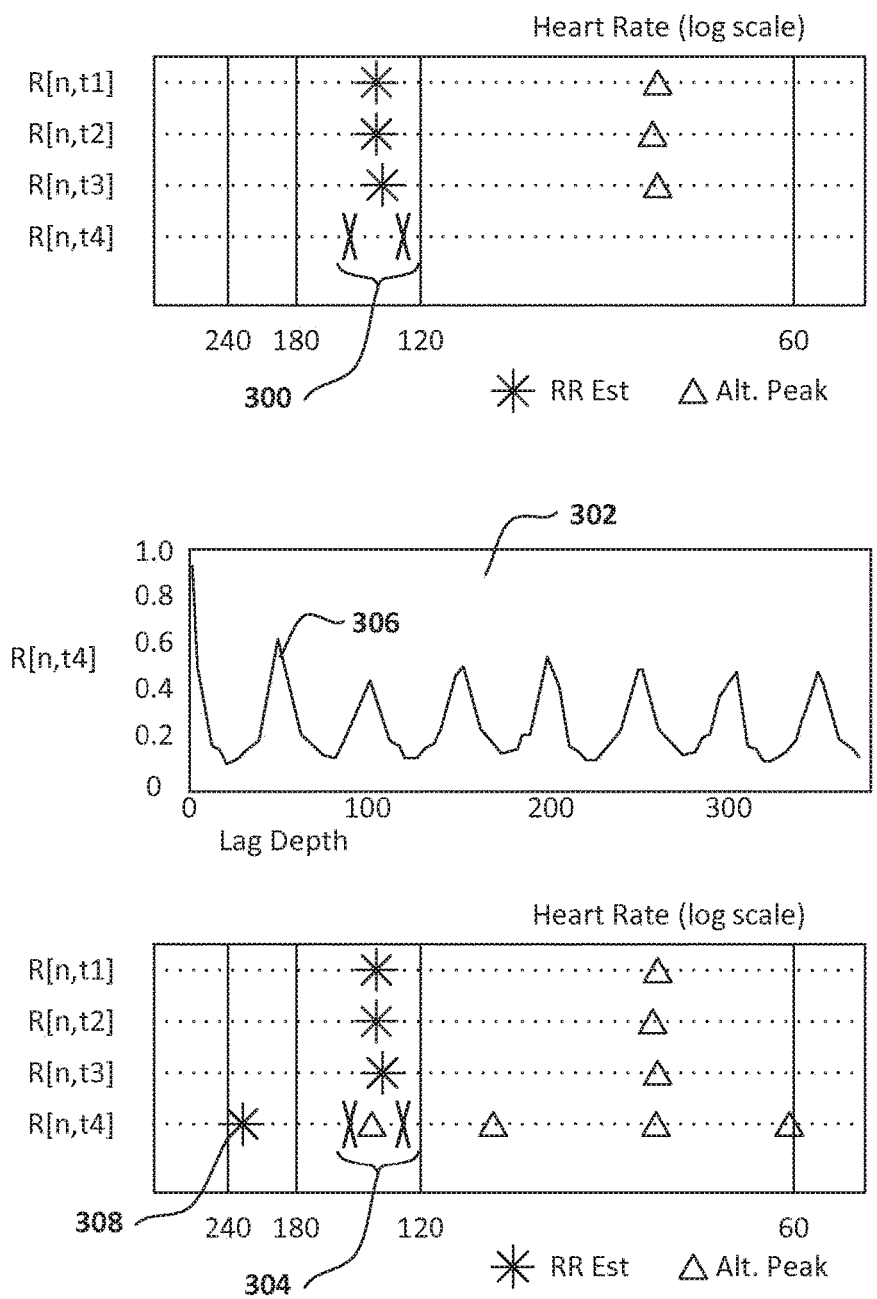

FIG. 13 presents another different scenario for the calculation of R[n,t4] after a track has been established. Gate 300 is set for the analysis, however, R[n,t4], as shown at 302, does not identify a peak that sits within the gate, as shown at 304, as the RR Estimate. Instead, a peak 306 at a lesser lag depth is identified as the RR Estimate. Thus the RR Estimate 308 sits away from the gate 304, though one of the alternate peaks in R[n,t4] is within the gate.

Referring back to FIG. 8B, the even shown in FIG. 13 would trigger a coasting analysis using the tachy jump limit 232. Specifically, RR Estimate 308 is at a relatively short lag depth shown, in the example, as corresponding to a rate between 180 and 240 bpm. Given this is the first such RR Estimate, not enough information is available yet to declare a new track. This could be a momentary jump, or it could be the onset of a new rhythm. Until more data is received, the illustrative method will wait and coast with the track continuing. The output rate estimate would continue to be within the existing track. However, because the RR Estimate is outside of the gate, any rate estimate would be reported with low confidence. A Tachy flag would be set based on the large peak in the tachy zone.

Figure 14:
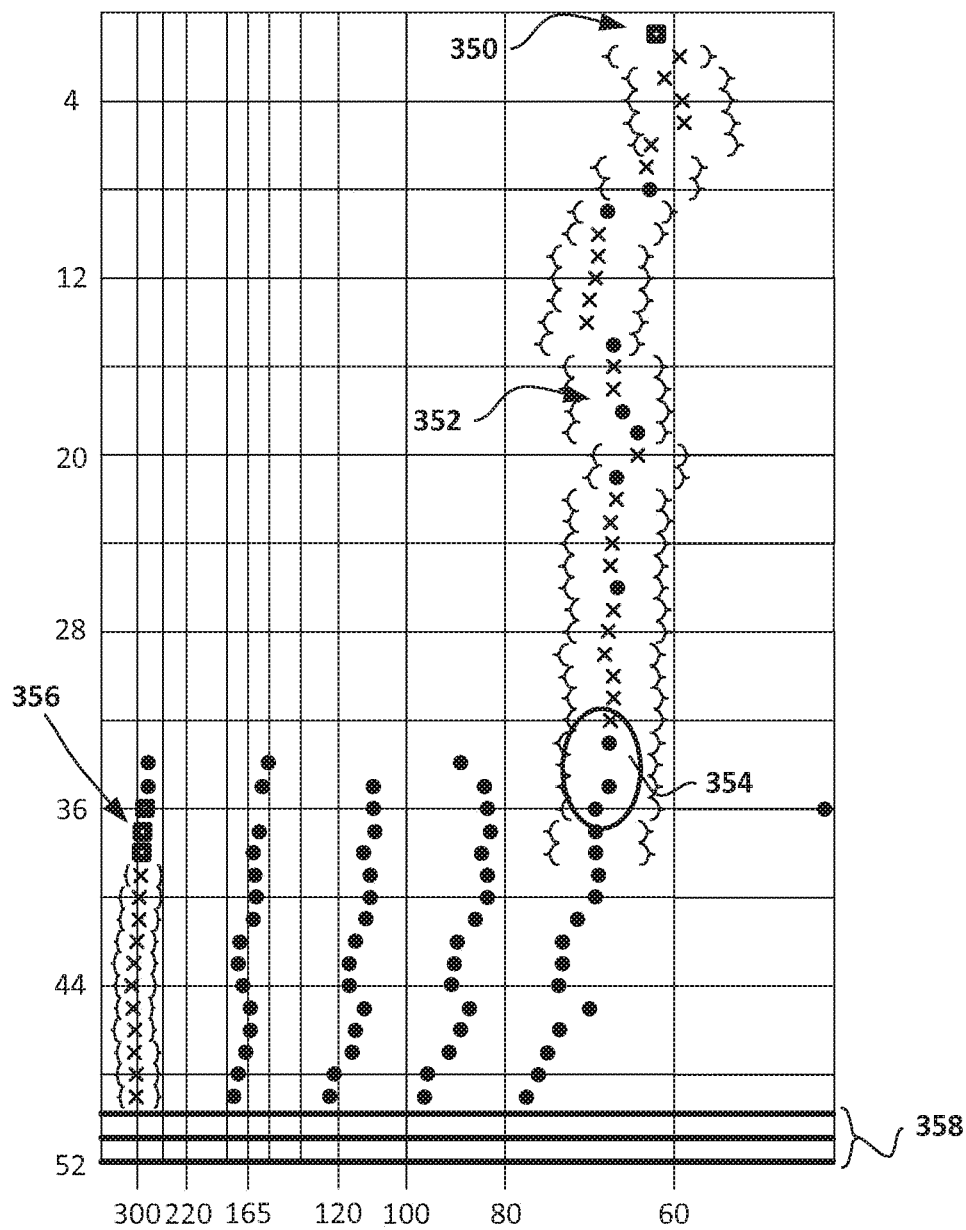
Figure 15:
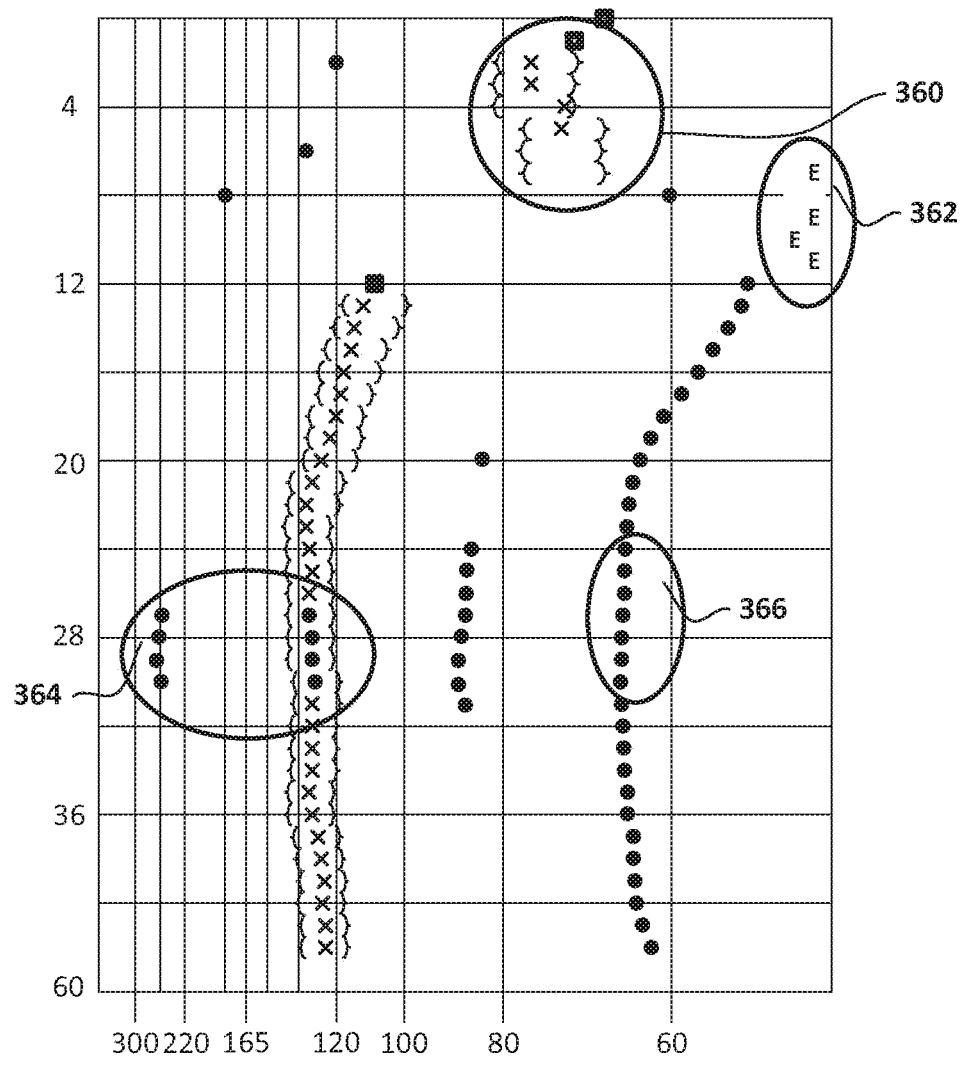

FIGS. 14 and 15 illustrate certain simulations of a system as described herein. In FIG. 14, the left side of the graph indicates time in seconds, while the horizontal axis is a log-scale of cardiac rate. Within the graph are the results of numerous self-correlation analyses.

Starting at 350, as indicated by the key at the bottom of the Figure, a high confidence peak is identified in a relatively low rate range (between 60-80 bpm). The received information from the self-correlation analysis stays generally in the track throughout the time period from 4 seconds until approximately 32 seconds. As noted at 352, there are some instances of coasting where the RR estimate is not within the gate—here, at 352, an alternate peak is identified in the gate and no RR estimate is generated, similar to what is shown in FIG. 13, above.

After 32 seconds, however, a very high rate arrhythmia starts. As shown at 354, during the transition from normal sinus to the high rate arrhythmia, the output of the self-correlation includes at least one instance where there is no alternate peak in the track. This may occur, for example, if no RR Estimate is generated as self-correlation occurs at a point in time where the buffer contains beats from two very different cardiac states. A sudden transition like this may happen at onset of VF, for example.

Additional alternate peaks appear in the gates at 35-38 seconds, however, by this point the only cardiac state reflected in the buffer is the VF. For this particular VF, the cardiac signal is repetitive, yielding RR Estimates at around 300 bpm. The boxes at 356 indicate the high rate RR Estimates. These high rate (short interval) RR Estimates cause trigger the Tachy Jump Limit 232 (FIG. 8B), and gates are applied starting at 39 seconds. Starting at 39 seconds, therefore, the self-correlation analysis confirms the high rate, treatable VF, which continues until therapy is delivered, as indicated by the bars across the self-correlation analysis during a therapy blanking period ranging from 50-52 seconds.

FIG. 15 illustrates another example, again with time on the vertical axis and rate on the horizontal axis. Initially, a track is declared after a couple of high confidence peaks, leading to tracking at 360. However, a noisy signal overall causes the track to become lost at 362, with the "E" designations indicating a lack of any viable peaks or RR estimate coming out of the analysis of R[n,t] during several iterations.

Subsequently, beginning with a very high confidence peak RR Estimate at about 12 seconds, a track is generated and followed for a period of time. Starting at about 26 seconds, and as highlighted at 364, a brief period occurs during which higher rate peaks become significant. This may occur, for example, if T-wave and R-wave peaks are fairly similar in amplitude while R-T and T-R intervals are similar. However, since both of these similarities are needed to sustain the higher rate peaks in R[n,t], the condition does not sustain for long. As a result, the tracker continues to keep the track going, relying upon the alternate peaks during the time period from 26-30 seconds to continue reporting a low to middle confidence rate. A tachy condition flag would be set, however, during this same time frame.

During the entire time from 12 seconds to 60 seconds, the lower rate pickets continue as shown at 366. These peaks not chosen as RR estimates in favor of the higher rate multiples that form the track.

As noted above, in a Bigemini pattern, there are two alternating morphologies for ventricular depolarization or "R" waves. A Bigemini pattern of ABAB will yield alternating peaks within the self-correlation result R[n]. High peaks will appear when "AB" is compared to "AB", with each of the A peaks aligned and each of the B peaks aligned, and relatively lower peaks when "AB" is compared to "BA", that is, A is compared to B and B to A. Within Bigemini patterns, however, the AB and BA intervals will often be consistent.

A cardiac signal with relatively large T-waves, when compared to R-waves, may appear somewhat similar to some Bigemini signals. This requires two elements: first, the R and T waves must be generally fairly similar, and second, the R-T and T-R intervals must also be fairly similar. The R-wave would usually be narrower than the T-wave, but if both are monophasic the two can be fairly similar. The R-T and T-R intervals are generally similar in only a narrow range of rates for any given patient. Moreover, as noted, for example, in U.S. Pat. Nos. 7,623,909 and 8,200,341, a sensing vector in which the R and T wave amplitudes are similar would often be disfavored from the outset, and vector selection can be used to choose a vector with a larger R:T amplitude ratio.

When a Bigemini pattern is analyzed using self-correlation, it can be difficult to determine whether the output reflects R-wave and T-wave peaks, which alternate and have different morphologies, or two R-waves having a Bigemini pattern. Vector selection can be used to avoid confusion, along with a set of rules shown and demonstrated in FIG. 16.

As shown at 400, a Bigemini rhythm, when subjected to the self-correlation analysis of FIGS. 4-5, above, yields a pattern of high and low peaks. Using the methods of FIGS. 6-7, above, would ordinarily select peak 402 as the RR Estimate peak. However, because the actual rhythm is a Bigemini signal, the true RR is at half the lag depth of the originally chosen RR Estimate, that is, at peak 404.

To address this potential issue, an optional Bigemini test is shown below at 408. The optional Bigemini test can be turned "on" by a physician, as not all patients are prone to this rhythm pattern.

The test begins after an RR Estimate has been calculated at 410. Next, the test looks for peaks spaced by one half of the lag depth of the RR Estimate, as shown at 412. As shown in the graphic at 400, peaks 404 and 406 meet the check at 412.

After passing the check at 412, the method determines whether the values of the R[n] peaks identified in block 412 are within a predetermined ratio of the value of the R[n] peak original selected as the RR estimate. "RVal" is used as the shorthand for the value of R[n] of each peak in the drawing. Here, a threshold is shown in the graphic 400, and peak 404 exceed the threshold, passing step 414. The illustrative threshold is 55% of the RVal peak for the original RR Estimate; other thresholds may be used in the range of, for example, 40-80%.

With both 412 and 414 passed, the Bigemini test will restate the RR Estimate, using the peak at RR Est/2 as shown at 416—here, peak 404 becomes RR Estimate. However, in light of the identification of a likely Bigemini pattern, for purposes of determining confidence in the outcome, the RVal for the original RR Estimate is retained, as indicated at 416. Thus, although peak 404 has an R[n] of about 0.5, the reported RVal figure would be about 0.75, R[n] value for peak 402.

If either of 412 or 414 fails, the Bigemini test fails as well, and the method ends at 418. Likewise, after any correction is made at block 416, the Bigemini test ends.

FIG. 17 addresses a test to check for jitter. Jitter may occur where the R-R interval is occasionally inconsistent, leading to a split peak in the output such as shown in the graphic at 430. Using the methods of FIGS. 6-7, an RR estimate is identified at 432. However, a split peak appears at 434, with the split peaks occurring at about RRest/2, with an R[n] value for each of the split peaks exceeding a relative threshold, suggesting that there may be jitter (or alternans, as the varying R-R intervals can be called) occurring.

To text for such jitter, a method is shown at 436. First, an RR Estimate is calculated, as shown at 438. Next the method checks for split peaks at RRest/2, as shown at 440. If such split peaks are found at 440, the method determines whether each of the split peaks meet an Rval threshold, as shown at 442. In the illustrative method, the Rval threshold is 50%; other thresholds may be used in the range of, for example, 40% to 80%.

If each of checks 440 and 442 are passed, then the method will restate the RR Estimate as RRest/2, as shown at 444. As with the bigemini test, the Rval from the original RRest can be retained in this example. If either of checks 440 and 442 fail, then the jitter test ends as shown at 446.

For each of the Bigemini test (FIG. 16) and Jitter test (FIG. 17), when the tests cause a modification of the RR Estimate, a flag may be set, a counter may be incremented, or the event may otherwise be counted/identified. In some examples, passing either of these tests can cause the system to store data in memory for later physician retrieval to review any such events.

Figure 18A:
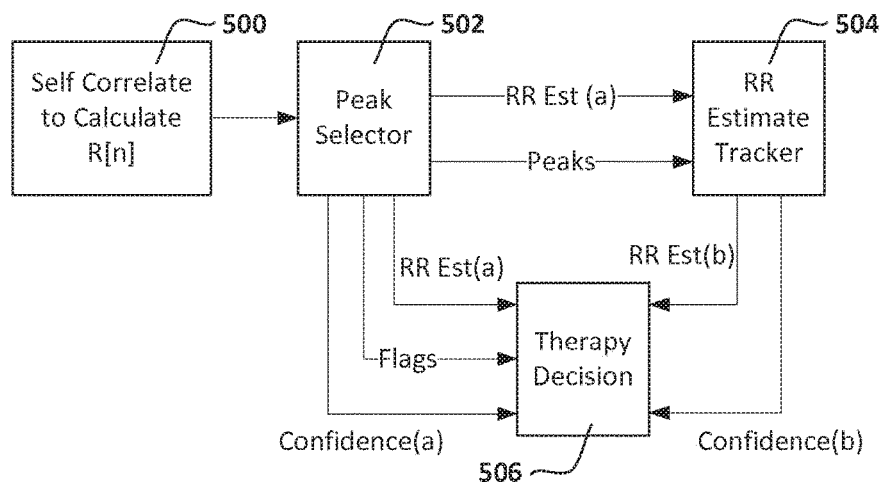
FIGS. 18A-18B illustrate different scenarios linking together the calculation of R[n], Peak Selector, Tracker, and Therapy Decision blocks.
Figure 18B:
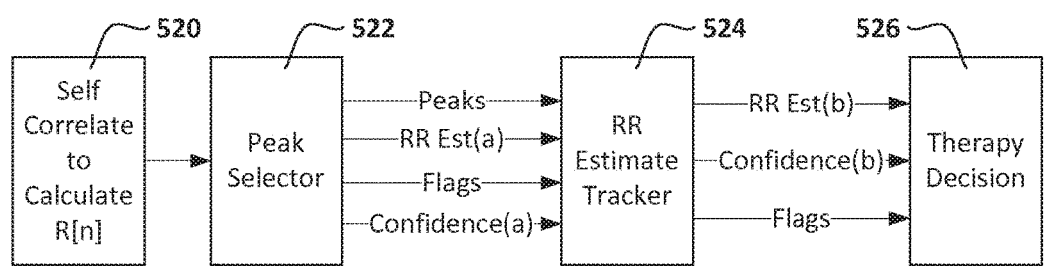

FIGS. 18A-18B show several ways in which the R[n] Calculator, a Peak Selector, an RR Estimate Tracker, and a Therapy Decision can be linked together. In the example of FIG. 18A, the R[n] Calculator 500 reports the output of an R[n] calculation to a Peak Selector 502. The Peak Selector 502 provides an RR Estimate(a) and a set of Peaks to the Peak Tracker 504. The Peak Selector 502 also provides, in this example, the RR Estimate(a) to a Therapy Decision Block 506, along with any Flags arising out of the Peak Selector 502 analysis as well as a Confidence(a) indicator. The Therapy Decision Block 506 can use the RR Estimate(a) from the Peak Selector 502 as well as any Flags and the Reported Confidence(a) to determine whether a conventional rate estimate is likely correct or incorrect. The RR Estimate Tracker 504 reports an RR Estimate(b) and Confidence to the Therapy Decision 506.

For example, the Peak Selector 502 may identify an RR Estimate(a), but with low Confidence(a), while the RR Estimate Tracker 504 identifies a different RR Estimate(b) with higher Confidence(b), based on a secondary peak that meets an existing Track and which either has one or more pickets or is in a tachy zone, even if the reported RR Estimate(a) is not in the track. In that case, the Therapy Decision block 506 may ignore the RR Estimate(a) and instead adopt RR Estimate(b).

In another example, if the RR Estimate(a) is reported with High Confidence(a), but the RR Estimate Tracker does not find a peak in an existing track and reports it is coasting, using a preserved, prior RR Estimate and reporting a low Confidence(b), the Therapy Decision block 506 may adopt RR Estimate(a) over RR Estimate (b).

Thus, in the example of FIG. 18A, Therapy Decision block 506 is allowed to select from between RR Estimate(a) and RR Estimate(b), using the reported Confidences from each of the Peak Selector 502 and RR Estimate Tracker 504.

In the example of FIG. 18B, the R[n] Calculator 520 again provides its results to the Peak Selector 522. The Peak Selector 522 performs its function and provides Peaks, an RR Estimate(a), any set Flags, and a Confidence(a) to the RR Estimate Tracker 524. The RR Estimate Tracker 524 performs its function and provides an RR Estimate(b), Confidence(b) and any set Flags to the Therapy Decision block 526. Thus, in FIG. 18B, the RR Estimate Tracker determines a single output RR Estimate(a) with associated Confidence(b) to the Therapy Decision block 526.

One or more of the individual blocks in FIGS. 18A-18B may be separate pieces of hardware in a single system, though two or more blocks may be integrated in a single dedicated circuit. Alternatively, the separate blocks in FIG. 18A-18B, may be separate functional blocks in a larger software structure. For example, given a stream (or stored stack) of data, a function call to Calculate R[n] 500/520 could be performed, followed by a function call to perform Peak Selection 502/522 given the output R[n], followed by a function call to Track RR Estimate 504/524 using the RR Estimate(a) and Peaks from Peak Selection, which may all be used as inputs (along with other data) for calling the Therapy Decision 506/526. In one example, blocks 500, 502 and 504 are provided on a dedicated circuit and the outputs of these blocks are provided to a processor or controller where the Therapy Decision process is performed.

In the embodiments shown in FIGS. 18A-18B (and other examples shown above and below), an RR Estimate can be considered an estimate of cardiac rate. Where a confidence measure is provided in association with an RR estimate and one or more peaks are detected, such can be treated as one or more possible estimates of cardiac rate.

Figure 19:
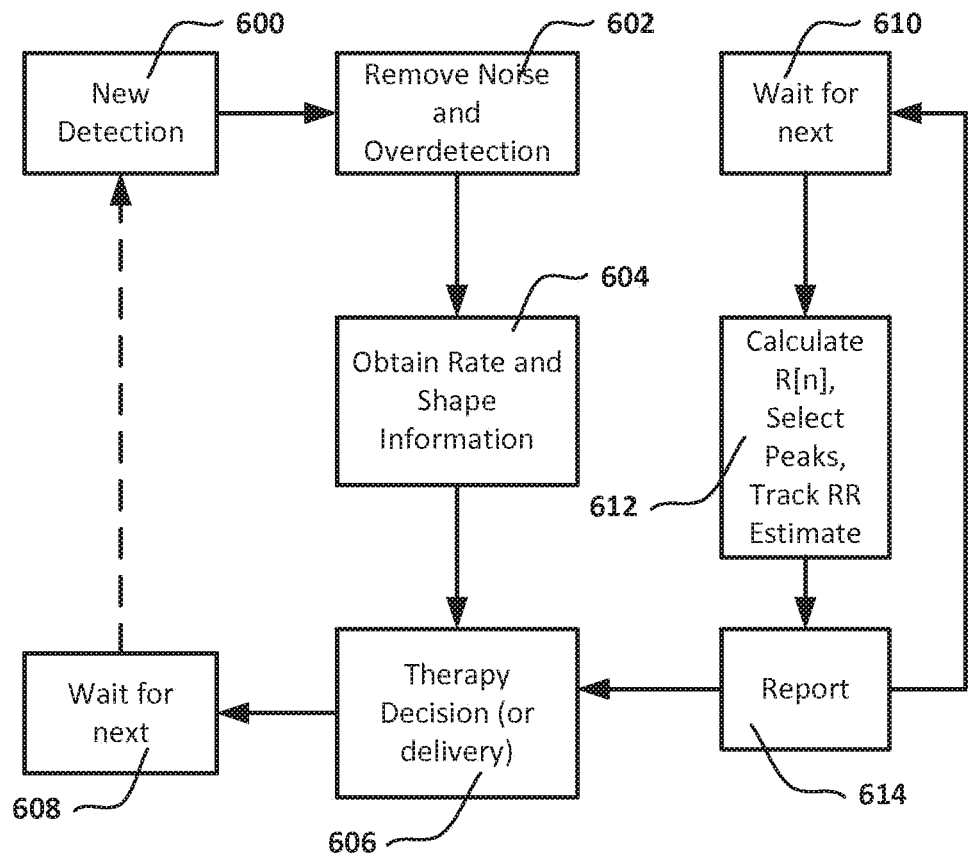
FIG. 19 is a block flow diagram for an overall method of cardiac signal analysis.

FIG. 19 illustrates an integration of two methods for identifying rate. A conventional rate method is illustrated using block 600, where R-waves are detected individually by comparing a detected signal to a threshold. Conventional R-wave detection may be used in block 600. Some illustrative examples appear in U.S. Pat. Nos. 8,565,878 and 5,709,215.

Detected R-waves are reported to a noise/overdetection removal block 602 which confirms the R-waves are likely cardiac events. Once the individually detected R-waves have been confirmed at 602, rate and shape (morphology) information are obtained 604 and provided to a therapy decision and/or delivery block 606. This conventional method then returns to a wait state 608 until the next R-wave detection.

The method also integrates a rate calculation using self-correlation, which can be called asynchronously (at fixed intervals, for example), or synchronously to the new detection 600, as desired. This wait state is depicted at 610. Upon activation, the self-correlation rate estimate is made using the combination one or more of calculating R[n], Selecting Peaks, and Tracking an RR Estimate 612. A resulting RR Estimate is then reported at 614 to the Therapy Decision block 606, and the wait state 610 is again entered.

The therapy decision 606 may use each of these different calculations in various approaches to identifying whether therapy is needed. For example, one of the rates may be used to double check the other, or the rates may be compared to identify a match. If the rates do not match, additional analysis may be performed using, for example, additional sensing inputs, such as a motion sensor or blood pressure or oxygenation sensor. If the rates both suggest therapy is needed (whether matching or not), therapy functions may then be called. Other approaches are noted above.

In some embodiments, a peak from R[n] may be considered the accurate rate and the rate as calculated by R-wave detection from block 600 ignored during at least a time period from a first calculation of R[n,t1] to a next calculation of R[n,t2]—that is, from time t1 to time t2, the R[n]-based rate is used instead of an R-wave detection based rate. In one example, if the dominant peak test is applied and met by a dominant peak, then therapy decision 606 may be configured to treat the estimated cardiac rate associated with the dominant peak as more reliable than a rate generated using an R-wave detection from block 600. In another example, a peak which passes the picket test may be treated in the therapy decision 606 as more reliable than a rate generated using an R-wave detection from block 600. In yet another example, the outputs of the peak selection may be treated as less reliable than the R-wave detection outputs until a track is declared via the methods of FIG. 8A-8B, and then only if the peak selection output falls within a defined track. In yet another example, if a viable track has been established or if a single, high confidence heart rate estimate is generated by the R[n] calculation, this will be used to override the R-wave based rate until the next calculation of R[n].

Still other examples may have multiple analytical courses depending on the status of the R-wave detection rate, tracking and peak selection outputs. For example, the following rules may apply in various examples:

If both R-wave detection rate and Self-Correlation Rate match and are high rates, the high rate is confirmed, suggesting tachyarrhythmia If R-wave detection suggests high rate but Self-Correlation Rate is lower, additional analysis is required (waiting time, detected event width or morphology analysis) before the high rate is treated as valid if either:
   the Self-Correlation Rate is based on a rate estimate falling within a valid track (the rate estimate being either a candidate or selected peak from peak analysis); or
   the Self-Correlation Rate is based on a selected peak that passes one of the picket test or the dominant peak test If R-wave detection rate is low, but Self-Correlation Rate is high, additional analysis (waiting time, detected event width or morphology analysis) is required before the high rate is treated as valid unless the Self-Correlation Rate is within a declared track and is based on a peak that passes the picket test (whether directly or via the large tachy peak test)

In another example, tracking is omitted and the following rules may apply:

The rate calculated using R-wave detection is treated as valid if it is high and the Self-Correlation rate exceeds a tachy threshold (whether the rates match or not);

The rate calculated using R-wave detection is treated as valid if it is high and the Self-Correlation test fails to meet either the picket test or dominant peak test;

The rate calculated using the Self-Correlation test is treated as valid if it is lower than the R-wave detection rate and below the tachy threshold and either passes the picket test or passes the dominant peak test Other combinations are also possible within the scope of the present invention.

The therapy decision 606 may determine whether the cardiac rate as estimated by one or both of blocks 602/612 exceeds a therapy threshold using, for example, a direct calculation of one rate, or a calculation across several iterations using one or more of an NID or X-out-of-Y filter as discussed above. The therapy decision may combine rate with morphology (shape) information gathered from the cardiac signal. In some examples, the therapy decision 606 can set two or more rate boundaries, including one or more of a shock-only boundary, in which rates above a threshold are deemed necessitating high energy cardioversion or defibrillation shock, a VT zone in which a lower energy therapy such as anti-tachycardia pacing is applied, and a conditional zone in which additional analysis of a combination of shape elements (template matching, width, interval stability, amplitude, etc.) as well as rate is performed.

The therapy decision 606 may integrate additional sensor inputs or inputs from separate devices, such as blood oxygenation, pressure, color, etc. measurements, measurements from a separate device such as a pressure monitor, leadless pacer, etc., or measurements from a position or movement sensor which can be separately provided in the patient's or integrated in a single device with the rest of the system that performs the self-correlation and other functions described above.

Various Notes & Examples

Each of these non-limiting examples can stand on its own, or can be combined in various permutations or combinations with one or more of the other examples.

A first non-limiting example takes the form of an implantable medical device system configured for iterative analysis of cardiac signals comprising a plurality of electrodes for sensing cardiac signals; self-correlation means for generating a self-correlation function from the sensed cardiac signals; peak selector means for identifying peaks in the self-correlation function and finding a first estimate of cardiac rate and first affiliated confidence having ratings of at least low or high confidence; tracking means for tracking peaks and cardiac rate estimates from the peak selector means over time and reporting a second estimate of cardiac rate with second affiliated confidence having ratings of at least low, medium or high confidence; and therapy decision means for using the first and second estimated cardiac rates and affiliated first and second confidences as reported by the peak selector means and the tracking means to decide whether a cardiac therapy is warranted. FIG. 3 and associated text illustrate the first non-limiting example by including a self-correlation means to generate the self-correlation function, R[n], at 60, a peak selector means at 62, and tracking means with blocks 64, 66 and 68 to generate an estimated rate and confidence at 70. Another example is in FIG. 18A, and associated text, with a self-correlation means at 500, peak selector means at 502, tracking means at 504, and therapy decision means at 506.

A second non-limiting example takes the form of an implantable medical device system as in the first non-limiting example wherein the tracking means is configured to observe whether a quantity of first estimates of cardiac rate from the peak selector means are similar to one another and, if so, to declare a first rate track.

A third non-limiting example takes the form of an implantable medical device system as in the second non-limiting example further configured such that, following establishment of the first rate track by the tracking means, if the peak selector provides a first estimate of cardiac rate meeting the first rate track, the tracking means is configured to report the second estimate of cardiac rate equal to the first estimate of cardiac rate with a high confidence.

A fourth non-limiting example takes the form of an implantable medical device system as in either of the second or third non-limiting examples wherein the peak selector means is configured to report, in addition to the first estimate of cardiac rate, one or more possible cardiac rates to the tracking means; and following establishment of the first rate track by the tracking means, if the peak selector provides a first estimate of cardiac rate that does not meet the first rate track, and no possible cardiac rate reported by the peak selector means meets the first rate track, the tracking means is configured to report the second estimate of cardiac rate unequal to the first estimate of cardiac rate and instead within the first rate track, with a low second affiliated confidence, unless a condition indicating the first rate track is no longer valid is met.

A fifth non-limiting example takes the form of an implantable medical device system as in either of the second or third non-limiting examples wherein the peak selector means is configured to report, in addition to the first estimate of cardiac rate, one or more possible cardiac rates to the tracking means; and following establishment of the first rate track by the tracking means, if the peak selector provides a first estimate of cardiac rate that does not meet the first rate track and a possible cardiac rate which does meet the first rate track, the tracking means is configured to report the second estimate of cardiac rate unequal to the first estimate of cardiac rate and instead within the first rate track, with a medium second affiliated confidence, unless a condition indicating the first rate track is no longer valid is met.

A sixth non-limiting example takes the form of an implantable medical device system as in either of the fourth or fifth non-limiting examples wherein the tracking means is configured to find a condition indicating the first rate track is no longer valid if: neither a first estimate of cardiac rate nor any possible cardiac rate reported by the peak selector means meets the first rate track for a first threshold duration; no first estimate of cardiac rate meets the first rate track for a second threshold duration; or a series of first estimates of cardiac rate reported by the peak selector means are both similar and do not meet the first rate track for a third threshold duration; wherein the first, second and third threshold durations take the form of either a quantity of iterations of analysis or a period of time; and wherein, if the third threshold duration is met, a new, second rate track, is declared using the series of first estimates of cardiac rate reported by the peak selector means which met the third threshold duration.

A seventh non-limiting example takes the form of an implantable medical device system as in any of the first to sixth non-limiting examples further comprising individual event detection means for identifying cardiac R-waves and generating a beat based rate estimate, wherein the therapy decision means uses at least one of the estimated cardiac rate or the beat based rate estimate to determine a likely cardiac rate for purposes of determine whether cardiac therapy is warranted.

An eighth non-limiting example takes the form of an implantable medical device system comprising: a plurality of electrodes for sensing cardiac signals; self-correlation means for generating a self-correlation function using the sensed cardiac signals; peak selector means for identifying peaks in the self-correlation function and finding one or more possible rate estimates and, when justified, a first estimated cardiac rate; tracking means for tracking outputs of the peak selector means over time and reporting a second estimated cardiac rate and affiliated confidence; and therapy decision means for using the estimated cardiac rate as reported by the tracking means to decide whether a cardiac therapy is warranted. FIG. 3 and associated text illustrate the first non-limiting example by including a self-correlation means to generate the self-correlation function, R[n], at 60, a peak selector means at 62, and tracking means with blocks 64, 66 and 68 to generate an estimated rate and confidence at 70. Another example is in FIG. 18B, and associated text, with a self-correlation means at 520, peak selector means at 522, tracking means at 524, and therapy decision means at 526.

A ninth non-limiting example takes the form of an implantable medical device system as in the eighth non-limiting example wherein the tracking means is configured to observe whether a quantity of first estimated cardiac rates from the peak selector means are similar to one another and, if so, to declare a first rate track.

A tenth non-limiting example takes the form of an implantable medical device system as in the ninth non-limiting example wherein, following establishment of the first rate track by the tracking means, if the peak selector means provides a first estimated cardiac rate meeting the first rate track, the tracking means is configured to report the second estimated cardiac rate equal to the first estimated cardiac rate with a high confidence.

An eleventh non-limiting example takes the form of an implantable medical device system as in either of the ninth or tenth non-limiting examples wherein, following establishment of the first rate track by the tracking means, if the peak selector provides a first estimated cardiac rate that does not meet the first rate track, and no possible rate estimate reported by the peak selector means meets the first rate track, the tracking means is configured to report the second estimated cardiac rate as a rate within the first rate track, with a low affiliated confidence, unless a condition indicating the first rate track is no longer valid is met.

A twelfth non-limiting example takes the form of an implantable medical device system as in either of the ninth or tenth non-limiting examples wherein, following establishment of the first rate track by the tracking means, if the peak selector provides a first estimate of cardiac rate that does not meet the first rate track and a possible rate estimate which does meet the first rate track, the tracking means is configured to report the second estimate of cardiac rate unequal to the first estimate of cardiac rate and instead report the possible rate estimate that is within the first rate track, with a medium affiliated confidence, unless a condition indicating the first rate track is no longer valid is met.

A thirteenth non-limiting example takes the form of an implantable medical device system as in either of the eleventh or twelfth non-limiting examples wherein the tracking means is configured to find a condition indicating the first rate track is no longer valid if: neither a first estimate of cardiac rate nor any possible rate estimate reported by the peak selector means meets the first rate track for a first threshold duration; no first estimate of cardiac rate meets the first rate track for a second threshold duration; or a series of first estimated cardiac rates reported by the peak selector means are both similar and do not meet the first rate track for a third threshold duration; wherein the first, second and third threshold durations take the form of either a quantity of iterations of analysis or a period of time; and wherein, if the third threshold duration is met, a new, second rate track is declared using the series of first estimates of cardiac rate reported by the peak selector means which met the third threshold duration.

A fourteenth non-limiting example takes the form of an implantable medical device system as in any of the eighth to thirteenth first non-limiting examples further comprising individual event detection means for identifying cardiac R-waves and generating a beat based rate estimate, wherein the therapy decision means uses at least one of the second estimated rate or the beat based rate estimate to determine a likely cardiac rate for purposes of determine whether cardiac therapy is warranted.

A fifteenth non-limiting example takes the form of an implantable medical device system as in any of the first through fourteenth non-limiting examples wherein the implantable medical device system comprises a canister housing operational circuitry including at least the self-correlation means, peak selector means, tracking means, and therapy decision means, and a lead system including at least some of the plurality of electrodes.

A sixteenth non-limiting example takes the form of a method of operation in an implantable cardiac device comprising: calculating a first estimate of cardiac rate; calculating a second estimate of cardiac rate and an associated confidence in the second estimate of cardiac rate; defining a boundary around the first estimate of cardiac rate; determining whether the second estimate of cardiac rate is within the boundary; and: if so, confirming the second estimate of cardiac rate as occurring with high confidence; or if not, identifying the second estimate of cardiac rate as occurring with low confidence.

A seventeenth non-limiting example takes the form of a method as in the sixteenth non-limiting example wherein the first and second estimates of cardiac rate are calculated by: establishing a buffer of cardiac data including a quantity of data samples; iteratively comparing at least a portion of the buffer of cardiac data to itself by shifting the quantity of data samples across the buffer to yield a function having peaks; selecting one of the peaks as representing a match; and determining how much shifting of the quantity of data samples is associated with the peak to calculate an RR interval.

An eighteenth non-limiting example takes the form of a method of operation in an implantable cardiac device comprising: analyzing cardiac data using a rate estimation method iteratively over time to yield a series of cardiac rate estimates; determining that the series of cardiac rate estimates establishing a first cardiac rate track; and following establishment of the first cardiac rate track, attempting a particular iteration of the rate estimation method and: determining that the cardiac data of the particular iteration fails to provide a cardiac rate; and interpolating a cardiac rate estimate using the first track.

A nineteenth non-limiting example takes the form of a method as in the eighteenth non-limiting example wherein the rate estimation method comprises: establishing a buffer of cardiac data including a quantity of data samples; iteratively comparing at least a portion of the buffer of cardiac data to itself by shifting the quantity of data samples across the buffer to yield a function having peaks; analyzing the peaks to determine whether any of the peaks alone represent a match of sufficient similarity to yield a reliable RR Estimate; analyzing the peaks to determine whether any combination of peaks represent a match of sufficient regularity to yield a reliable RR Estimate; and if either analysis of the peaks yields a reliable RR Estimate, determining an RR Estimate; wherein, for the particular iteration, neither analysis of the peaks yields a reliable RR estimate.

A twentieth non-limiting example takes the form of a method as in either of the eighteenth or nineteenth non-limiting examples wherein the step of interpolating a cardiac rate further requires that the rate estimation method identify a possible cardiac rate matching the first track.

A twenty-first non-limiting example takes the form of a method of cardiac signal analysis in an implantable medical device system comprising a plurality of electrodes for sensing cardiac signals coupled to operational circuitry configured to analyze signals generated by the plurality of electrodes, the method comprising: sensing cardiac signals using the plurality of electrodes; iteratively performing a self-correlation to generate a self-correlation function using the sensed cardiac signals; for a plurality of iterations of the self-correlation, identifying peaks in the self-correlation function to yield a first estimate of cardiac rate and first affiliated confidence having ratings of at least low or high confidence, except if no peak can be identified sufficient to yield an estimate of cardiac rate; tracking peaks and cardiac rate estimates generated by the identifying peaks step over time to yield a second estimate of cardiac rate with second affiliated confidence having ratings of at least low, medium or high confidence, in which the second estimate of cardiac rate may or may not match the first estimate of cardiac rate; and using the first and second estimated cardiac rates and affiliated first and second confidences to decide whether a cardiac therapy is warranted.

A twenty-second non-limiting example takes the form of a method as in the twenty-first non-limiting example wherein the step of tracking peaks and cardiac rate estimates includes determining whether a quantity of first estimates of cardiac rate are similar to one another and, if so, to declaring a first rate track.

A twenty-third non-limiting example takes the form of a method as in either of the twenty-first or twenty-second non-limiting examples wherein, following declaration of the first rate track, the tracking step includes determining whether, in a subsequent iteration, a first estimate of cardiac rate meets a rule associated with the first rate track, and, if so, reporting the second estimate of cardiac rate as a rate equal to the first estimate of cardiac rate, and with a high confidence.

A twenty-fourth non-limiting example takes the form of a method as in any of the twenty-first through twenty-third non-limiting examples wherein: during iterations of the step of identifying peaks, in addition to reporting the first estimate of cardiac rate, one or more possible cardiac rates are identified by analysis of the self-correlation function; following declaration of the first rate track, the tracking step includes determining whether, in a subsequent iteration: a) a first estimate of cardiac rate does not meet a rule associated with the first rate track, and b) no possible cardiac rate identified by analysis of the self-correlation meets the rule associated with the first rate track, either; then, if both a) and b) are true, the tracking step includes reporting a second estimate of cardiac rate which is both unequal to the first estimate of cardiac rate and falls within the first rate track, with a low second affiliated confidence, unless a condition indicating the first rate track is no longer valid is met.

A twenty-fifth non-limiting example takes the form of a method as in the twenty-fourth non-limiting example wherein a condition indicating the first rate track is not longer valid is met if both a) and b) remain true for at least a predetermined quantity of consecutive iterations.

A twenty-sixth non-limiting example takes the form of a method as in any of the twenty-first through twenty-third non-limiting examples wherein, during iterations of the step of identifying peaks, in addition to reporting the first estimate of cardiac rate, one or more possible cardiac rates are identified by analysis of the self-correlation function; following declaration of the first rate track, the tracking step includes determining whether, in a subsequent iteration: a) a first estimate of cardiac rate does not meet a rule associated with the first rate track, and b) a possible cardiac rate identified by analysis of the self-correlation function does meet the rule associated with the first rate track; then, if both a) and b) are true, the tracking step includes reporting a second estimate of cardiac rate which is unequal to the first estimate of cardiac rate and instead matches the possible cardiac rate used in b), with a medium confidence.

A twenty-seventh non-limiting example takes the form of a method as in any of the twenty-first through twenty-sixth non-limiting examples, further comprising determining that the first rate track is no longer valid if no first estimate of cardiac rate meets a rule associated with the first rate track for a predetermined period of time or number of iterations.

A twenty-eighth non-limiting example takes the form of a method as in any of the twenty-first through twenty-seventh non-limiting examples, further comprising identifying a jump from the first rate track to a second rate track if, over a series of iterations, at least a predetermined number of first estimates of cardiac rate are similar to one another and do not meet a rule associated with the first rate track.

A twenty-ninth non-limiting example takes the form of a method as in any of the twenty-first through twenty-eighth non-limiting examples, further comprising comparing a detection threshold to the sensed cardiac signals to identify individual cardiac cycles and generate a third estimate of cardiac rate; wherein the step of using the first and second estimated cardiac rates and affiliated first and second confidences to decide whether a cardiac therapy is warranted further comprises: determining which of the first, second and third estimated cardiac rates is likely the most reliable, and using the likely most reliable estimated cardiac rate to decide whether a cardiac therapy is warranted.

A thirtieth non-limiting example takes the form of a method of cardiac signal analysis in an implantable medical device system comprising a plurality of electrodes for sensing cardiac signals coupled to operational circuitry configured to analyze signals generated by the plurality of electrodes, the method comprising: sensing cardiac signals using the plurality of electrodes; iteratively performing a self-correlation to generate a self-correlation function using the sensed cardiac signals; for a plurality of iterations of the self-correlation, identifying peaks in the self-correlation function to yield a first estimate of cardiac rate and one or more possible cardiac rates, except if no peak can be identified sufficient to yield an estimate of cardiac rate; tracking peaks and cardiac rate estimates generated by the identifying peaks step over time to yield a second estimate of cardiac rate with an affiliated confidence having ratings of at least low, medium or high confidence; and using the second estimated cardiac rate and affiliated confidence to decide whether a cardiac therapy is warranted.

A thirty-first non-limiting example takes the form of a method as in the thirtieth non-limiting example, wherein the step of tracking peaks and cardiac rate estimates includes determining whether a quantity of first estimates of cardiac rate are similar to one another and, if so, to declaring a first rate track.

A thirty-second non-limiting example takes the form of a method as in the thirty-first non-limiting example, wherein, following declaration of the first rate track, the tracking step includes determining whether, in a subsequent iteration, a first estimate of cardiac rate meets a rule associated with the first rate track, and, if so, reporting the second estimate of cardiac rate as a rate equal to the first estimate of cardiac rate, and with a high confidence.

A thirty-third non-limiting example takes the form of a method as in either of the thirty-first or thirty-second non-limiting examples wherein: following declaration of the first rate track, the tracking step includes determining whether, in a subsequent iteration: a) a first estimate of cardiac rate does not meet a rule associated with the first rate track, and b) no possible cardiac rate identified by analysis of the self-correlation meets the rule associated with the first rate track, either; then, if both a) and b) are true, the tracking step includes reporting a second estimate of cardiac rate which is both unequal to the first estimate of cardiac rate and falls within the first rate track, with a low second affiliated confidence, unless a condition indicating the first rate track is no longer valid is met.

A thirty-fourth non-limiting example takes the form of a method as in either of the thirty-first or thirty-second non-limiting examples wherein: following declaration of the first rate track, the tracking step includes determining whether, in a subsequent iteration: a) a first estimate of cardiac rate does not meet a rule associated with the first rate track, and b) a possible cardiac rate identified by analysis of the self-correlation function does meet the rule associated with the first rate track; then, if both a) and b) are true, the tracking step includes reporting a second estimate of cardiac rate which is unequal to the first estimate of cardiac rate and instead matches the possible cardiac rate used in b), with a medium confidence.

A thirty-fifth non-limiting example takes the form of a method as in either of the thirty-first or thirty-second non-limiting examples, further comprising: comparing a detection threshold to the sensed cardiac signals to identify individual cardiac cycles and generate a third estimate of cardiac rate; wherein the step of using the first and second estimated cardiac rates and affiliated first and second confidences to decide whether a cardiac therapy is warranted further comprises: determining which of the first, second and third estimated cardiac rates is likely the most reliable, and using the likely most reliable estimated cardiac rate to decide whether a cardiac therapy is warranted.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable cardiac system comprising a canister housing operational circuitry, the operational circuitry being configured for use with a plurality of electrodes, the operational circuitry being configured to operate in a manner comprising:
sensing cardiac signals by receiving electrical signals from the plurality of electrodes;
analyzing the sensed cardiac signals using a rate estimation method iteratively over time to yield a series of cardiac rate estimates;
determining that the series of cardiac rate estimates establishes a first cardiac rate track; and
following establishment of the first cardiac rate track, attempting a particular iteration of the rate estimation method and:
determining that the particular iteration fails to provide a cardiac rate; and
interpolating a cardiac rate estimate using the first track.

2. A system as in claim 1 wherein the operational circuitry is configured to perform the rate estimation method comprising:
establishing a buffer of cardiac data from the sensed cardiac signals including a quantity of data samples;
iteratively comparing at least a portion of the buffer of cardiac data to itself by shifting the quantity of data samples across the buffer to yield a function having peaks;
analyzing the peaks to determine whether any of the peaks alone represent a match of sufficient similarity to yield a reliable cardiac rate estimate; and
analyzing the peaks to determine whether any combination of peaks represent a match of sufficient regularity to yield a reliable cardiac rate estimate.

3. A system as in claim 1 wherein the operational circuitry is configured such that the step of interpolating a cardiac rate using the first track is performed by confirming that the rate estimation method has identified a possible cardiac rate matching the first track.

4. An implantable cardiac defibrillator taking the form of a system as recited in claim 1 and further comprising therapy delivery circuitry including a capacitor and charger circuit for generating, and output circuitry for delivering defibrillation therapy.

5. A system as in claim 1 wherein the operational circuitry is configured for analyzing far-field cardiac signals from an implanted location distant from the heart.

6. An implantable cardiac system comprising a canister housing operational circuitry, the operational circuitry being configured for use with a plurality of electrodes, the operational circuitry being configured to operate in a manner comprising:
sensing cardiac signals using the plurality of electrodes;
iteratively performing a self-correlation to generate a self-correlation function using the sensed cardiac signals;
for a plurality of iterations of the self-correlation, identifying peaks in the self-correlation function to yield a first estimate of cardiac rate and first affiliated confidence having ratings of at least low or high confidence, except if no peak can be identified sufficient to yield an estimate of cardiac rate;
tracking peaks and cardiac rate estimates generated by the identifying peaks step over time to yield a second estimate of cardiac rate with second affiliated confidence having ratings of at least low, medium or high confidence, in which the second estimate of cardiac rate may or may not match the first estimate of cardiac rate; and
using the first and second estimated cardiac rates and affiliated first and second confidences to decide whether a cardiac therapy is warranted.

7. A system as in claim 6 wherein the operational circuitry is configured such that the step of tracking peaks and cardiac rate estimates includes determining whether a quantity of first estimates of cardiac rate are similar to one another and, if so, declaring a first rate track.

8. A system as in claim 7 wherein the operational circuitry is configured such that, following declaration of the first rate track, the tracking step includes determining whether, in a subsequent iteration, a first estimate of cardiac rate meets a rule associated with the first rate track, and, if so, reporting the second estimate of cardiac rate as a rate equal to the first estimate of cardiac rate, and with a high confidence.

9. A system as in claim 7 wherein the operational circuitry is further configured such that:
during iterations of the step of identifying peaks, in addition to reporting the first estimate of cardiac rate, one or more possible cardiac rates are identified by analysis of the self-correlation function;
following declaration of the first rate track, the tracking step includes determining whether, in a subsequent iteration:
a) a first estimate of cardiac rate does not meet a rule associated with the first rate track, and
b) no possible cardiac rate identified by analysis of the self-correlation meets the rule associated with the first rate track, either;
then, if both a) and b) are true, the tracking step includes reporting a second estimate of cardiac rate which is both unequal to the first estimate of cardiac rate and falls within the first rate track, with a low second affiliated confidence, unless a condition indicating the first rate track is no longer valid is met.

10. A system as in claim 9 wherein the operational circuitry is further configured such that a condition indicating the first rate track is no longer valid is met if both a) and b) remain true for at least a predetermined quantity of consecutive iterations.

11. A system as in claim 7 wherein the operational circuitry is further configured such that:
during iterations of the step of identifying peaks, in addition to reporting the first estimate of cardiac rate, one or more possible cardiac rates are identified by analysis of the self-correlation function;
following declaration of the first rate track, the tracking step includes determining whether, in a subsequent iteration:
a) a first estimate of cardiac rate does not meet a rule associated with the first rate track, and
b) a possible cardiac rate identified by analysis of the self-correlation function does meet the rule associated with the first rate track;
then, if both a) and b) are true, the tracking step includes reporting a second estimate of cardiac rate which is unequal to the first estimate of cardiac rate and instead matches the possible cardiac rate used in b), with a medium confidence.

12. A system as in claim 7 wherein the operational circuitry is further configured to operate by determining that the first rate track is no longer valid if no first estimate of cardiac rate meets a rule associated with the first rate track for a predetermined period of time or number of iterations.

13. A system as in claim 7 wherein the operational circuitry is further configured to operate by identifying a jump from the first rate track to a second rate track if, over a series of iterations, at least a predetermined number of first estimates of cardiac rate are similar to one another and do not meet a rule associated with the first rate track.

14. A system as in claim 6 wherein the operational circuitry is further configured to operate by:
comparing a detection threshold to the sensed cardiac signals to identify individual cardiac cycles and generate a third estimate of cardiac rate;
wherein the step of using the first and second estimated cardiac rates and affiliated first and second confidences to decide whether a cardiac therapy is warranted further comprises:
determining which of the first, second and third estimated cardiac rates is likely the most reliable, and
using the likely most reliable estimated cardiac rate to decide whether a cardiac therapy is warranted.

15. An implantable cardiac system comprising a canister housing operational circuitry, the operational circuitry being configured for use with a plurality of electrodes, the operational circuitry being configured to operate in a manner comprising:
sensing cardiac signals using the plurality of electrodes;
iteratively performing a self-correlation to generate a self-correlation function using the sensed cardiac signals;
for a plurality of iterations of the self-correlation, identifying peaks in the self-correlation function to yield a first estimate of cardiac rate and one or more possible cardiac rates, except if no peak can be identified sufficient to yield an estimate of cardiac rate;
tracking peaks and cardiac rate estimates generated by the identifying peaks step over time to yield a second estimate of cardiac rate with an affiliated confidence having ratings of at least low, medium or high confidence; and
using the second estimated cardiac rate and affiliated confidence to decide whether a cardiac therapy is warranted.

16. A system as in claim 15 wherein the operational circuitry is further configured such that the step of tracking peaks and cardiac rate estimates includes determining whether a quantity of first estimates of cardiac rate are similar to one another and, if so, to declaring a first rate track.

17. A system as in claim 16 wherein the operational circuitry is further configured such that, following declaration of the first rate track, the tracking step includes determining whether, in a subsequent iteration, a first estimate of cardiac rate meets a rule associated with the first rate track, and, if so, reporting the second estimate of cardiac rate as a rate equal to the first estimate of cardiac rate, and with a high confidence.

18. A system as in claim 16 wherein the operational circuitry is further configured such that, following declaration of the first rate track, the tracking step includes determining whether, in a subsequent iteration:
a) a first estimate of cardiac rate does not meet a rule associated with the first rate track, and
b) no possible cardiac rate identified by analysis of the self-correlation meets the rule associated with the first rate track, either;
then, if both a) and b) are true, the tracking step includes reporting a second estimate of cardiac rate which is both unequal to the first estimate of cardiac rate and falls within the first rate track, with a low second affiliated confidence, unless a condition indicating the first rate track is no longer valid is met.

19. A system as in claim 16 wherein the operational circuitry is further configured such that the manner of operation further comprises:
following declaration of the first rate track, the tracking step includes determining whether, in a subsequent iteration:
a) a first estimate of cardiac rate does not meet a rule associated with the first rate track, and
b) a possible cardiac rate identified by analysis of the self-correlation function does meet the rule associated with the first rate track;
then, if both a) and b) are true, the tracking step includes reporting a second estimate of cardiac rate which is unequal to the first estimate of cardiac rate and instead matches the possible cardiac rate used in b), with a medium confidence.

20. A system as in claim 16 wherein the operational circuitry is further configured such that the manner of operation further comprises:
comparing a detection threshold to the sensed cardiac signals to identify individual cardiac cycles and generate a third estimate of cardiac rate;
wherein the step of using the first and second estimated cardiac rates and affiliated first and second confidences to decide whether a cardiac therapy is warranted further comprises:
determining which of the first, second and third estimated cardiac rates is likely the most reliable, and
using the likely most reliable estimated cardiac rate to decide whether a cardiac therapy is warranted.

* * * * *